US005654448A

United States Patent [19]
Pandey et al.

[11] Patent Number: 5,654,448
[45] Date of Patent: Aug. 5, 1997

[54] ISOLATION AND PURIFICATION OF PACLITAXEL FROM ORGANIC MATTER CONTAINING PACLITAXEL, CEPHALOMANNINE AND OTHER RELATED TAXANES

[75] Inventors: Ramesh C. Pandey, Highland Park; Luben K. Yankov, Edison, both of N.J.

[73] Assignee: Xechem International, Inc., New Brunswick, N.J.

[21] Appl. No.: 572,240

[22] Filed: Dec. 13, 1995

Related U.S. Application Data

[63] Continuation-in-part of Ser. No. 530,846, Oct. 2, 1995.
[51] Int. Cl.$^6$ ................................................ C07D 305/14
[52] U.S. Cl. .................................. 549/510; 549/511
[58] Field of Search ................................ 549/510, 511

[56] References Cited

U.S. PATENT DOCUMENTS

| | | | |
|---|---|---|---|
| 4,814,470 | 3/1989 | Colin et al. | 514/449 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,175,315 | 12/1992 | Holton | 549/510 |
| 5,194,635 | 3/1993 | Kingston et al. | 549/430 |
| 5,200,534 | 4/1993 | Rao | 549/510 |
| 5,202,448 | 4/1993 | Carver et al. | 549/510 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,248,796 | 9/1993 | Chen et al. | 549/510 |
| 5,250,683 | 10/1993 | Holton et al. | 544/65 |
| 5,250,722 | 10/1993 | Bombardelli et al. | 560/104 |
| 5,254,580 | 10/1993 | Chen et al. | 514/449 |
| 5,254,703 | 10/1993 | Holton | 549/510 |
| 5,272,171 | 12/1993 | Ueda et al. | 514/449 |
| 5,274,124 | 12/1993 | Holton | 549/214 |
| 5,278,324 | 1/1994 | Kingston et al. | 549/510 |
| 5,279,949 | 1/1994 | Nair | 435/123 |
| 5,283,253 | 2/1994 | Holton et al. | 514/444 |
| 5,284,864 | 2/1994 | Holton et al. | 514/449 |
| 5,284,865 | 2/1994 | Holton et al. | 514/449 |
| 5,294,637 | 3/1994 | Chen et al. | 514/449 |
| 5,296,506 | 3/1994 | Kingston et al. | 514/449 |
| 5,300,638 | 4/1994 | Farina et al. | 540/357 |
| 5,310,672 | 5/1994 | Wann et al. | 435/240 |
| 5,319,112 | 6/1994 | Kingston et al. | 549/510 |
| 5,334,732 | 8/1994 | Murray et al. | 549/510 |
| 5,336,684 | 8/1994 | Murray et al. | 514/449 |
| 5,336,785 | 8/1994 | Holton | 549/214 |
| 5,338,872 | 8/1994 | Holton et al. | 549/510 |
| 5,412,092 | 5/1995 | Rey et al. | 540/200 |
| 5,470,866 | 11/1995 | Kingston et al. | 514/376 |
| 5,473,055 | 12/1995 | Mongelli et al. | 530/329 |
| 5,475,011 | 12/1995 | Ojima et al. | 514/320 |
| 5,475,120 | 12/1995 | Rao | 549/510 |

*Primary Examiner*—Ba K. Trinh
*Attorney, Agent, or Firm*—Duane, Morris & Heckscher

[57] ABSTRACT

A novel process for extraction, isolation and separation of taxanes, particularly paclitaxel, from natural sources such as bark, needles and twigs from Taxus species, tissue cultures, and fungi is described, wherein the taxanes are separated from the crude extracts by partitioning between polar and nonpolar solvents, precipitation in nonpolar solutions, reacting the mixture by halogenation of unsaturated taxane derivatives, followed by chromatographically separating and crystallizing taxanes from a mixture of polar and nonpolar solvents; more particularly, the process of halogenation of unsaturated side chain taxane derivatives, particularly cephalomannine in presence of paclitaxel, is described, wherein bromine is preferably added to the double bond of unsaturated taxanes leaving paclitaxel unchanged, with paclitaxel being easily separated from the mixture including the less polar halogenated taxane derivatives.

34 Claims, 16 Drawing Sheets

PACLITAXEL

CEPHALOMANNINE

ISOLATION AND PURIFICATION OF PACLITAXEL FROM ORGANIC MATTER CONTAINING PACLITAXEL, CEPHALOMANNINE AND OTHER RELATED TAXANES

This application is a continuation in part of application U.S. Ser. No. 08/530,846, filed Oct. 2, 1995, now pending.

FIELD OF THE INVENTION

This invention relates to the isolation and purification of paclitaxel from any source containing paclitaxel, including organic matter such as plant material, cultures and fungi, and in particular from *T. brevifolia*, the bark of the Pacific Yew tree and *T. baccata, T. yunnanensis, T. walichiana*. More particularly, this invention provides for the separation and purification of paclitaxel from mixtures of taxanes containing various concentrations of paclitaxel and other taxanes, including closely related taxanes having unsaturated side chains such as cephalomannine.

BACKGROUND OF THE INVENTION

Paclitaxel is a well known chemotherapeutic drug for treatment of various metastatic cancers. It has been approved by the Food and Drag Administration (FDA) for the treatment of ovarian and breast cancers and is currently in clinical trials for the treatment of lung and colon cancers.

The compound is a natural product primarily extracted from the bark of the Pacific Yew tree, *Taxus brevifolia*, and is also found in *T. baccata, T. walichiana* and *T. yunnanensis* and other biomass extracts from plant materials including *T. hicksii, T. densiformis, T. gem, T. wardii, T. cuspidata, T. capitata, T. brownii*, and T. dark green spreader, which contain a mixture of taxane-type molecules. Paclitaxel is also available from cultured plant cells and fungi. The compound is commercially available in reagent grade, for example, from the Aldrich Chemical Co., product No. 41,701-7, Sigma Chemical Company, product Nos. T 7402 and T 1912, depending on the source it was derived from, Fluka Chemie AG. product No. 86346 and ICN Biomedicals product No. 193532.

The concentration of paclitaxel in various raw materials is typically low, for example, on the order of between 0.0004-0.08% (w/w) in the bark of the Pacific Yew. Such low concentrations render the extraction and purification of the compound to clinical standards from raw materials very challenging, and heretofore impractical on a commercial level.

Presently, several processes for the extraction and purification of paclitaxel are known. Wani et al., J. Am. Chem. Soc. 93,9:2325-2327 (1971), describes extraction of *T. brevifolia* stem bark with ethanol, which is then concentrated and extracted with chloroform and water, and wherein the paclitaxel is found in the chloroform phase. The paclitaxel is further purified by column chromatography over florisil, sephadex, and silica gel columns.

A National Cancer Institute (NCI) method (1983) is based on extraction of *T. brevifolia* stem bark with methanol followed by methylene chloride extraction. The methylene chloride extract is dried and then dissolved in acetone followed by precipitation of impurities with n-hexane. The soluble fraction is further purified by column chromatography.

Both the Wani et al. and NCI procedures, however, are not very efficient or commercially practical as they result in very low yields on the order of about 0.02% or less. This is due to the presence of other taxanes, such as paclitaxel's close analog cephalomannine, having similar structures and very close physical properties to that of paclitaxel. See FIG. 1 which illustrates the chemical structures of paclitaxel and cephalomannine.

In a process developed by Potier et al., J. Nat. Prod., 47,1:131-137 (1984), the precipitation step in the NCI process is substituted for a step employing a solvent pair extraction method, i.e. using successive extractions with progressively increasing polar solvents. After further steps of chromatography over alumina and silica columns, the paclitaxel is concentrated as a mixture of paclitaxel and cephalomannine. The paclitaxel is then separated from cephalomannine by HPLC, with a yield of paclitaxel considerably higher than obtained by either of the Wani et al. or NCI methods.

However, the Potier et al. method, in similar manner as the Wani et al. and NCI methods, suffers from the major drawback of requiring the separation of multiple taxanes with similar separation parameters in a final concentrate by the use of multiple conventional chromatographic separations to obtain a purified paclitaxel product. As large scale commercial processing of paclitaxel employing multiple conventional chromatographic separations to provide clinically acceptable pure paclitaxel would be necessitated by these methods, such are commercially impractical because of the large expense associated with such multiple chromatographic separations.

Multiple separations are necessitated for the most part by the similarity in both structure and properties of paclitaxel with cephalomannine. As shown in FIG. 1, the only difference in their structures is that the amino group in the side chain in paclitaxel is acylated with benzoic acid, and in cephalomannine the side chain amino group is acylated with tiglic acid containing a double bond.

Methods other than chromatographic separation of paclitaxel from cephalomannine are known, such as chemical modifications of the side chain double bond in cephalomannine. For example, Kingston, et al., J. Nat. Prod., 55: No. 2, 259-261 (1992) describes the catalytic oxidation of the cephalomannine side chain double bond in the presence of $OsO_4$ to obtain a diol, which is then separated from paclitaxel by chromatographic procedures and recrystallizations. There are problems with this method in the use of unpurified taxane mixtures since the oxidation catalyzed by $OsO_4$ is not amenable to crude extracts due to low selectivity for the side chain double bond of cephalomannine, which if could be used, would significantly reduce the cost of the extraction and purification process. Additionally, using $OsO_4$ in the manufacture of pharmaceuticals is not desirable due to the severe toxicity of the compound.

In U.S. Pat. Nos. 5,334,732 and 5,336,684 to Murray, et al., oxidation of the cephalomannine side chain by ozone is described. These methods are also undesirable in that the use of ozone in an oxidation process with crude extracts produces many unwanted reactions with paclitaxel; oxidation by ozonolysis is strong and not selective in compounds with many functional groups such as paclitaxel and cephalomannine, and may cause unwanted oxidations of other functional groups, such as aldehydes, ketones, amines, etc. in the paclitaxel molecule or of the double bond found on the inside of the taxane ting of either paclitaxel or cephalomannine. There is also the expensive requirement of an ozone generator.

Thus, the isolation and purification of paclitaxel from a raw biomass-containing complex mixture of taxanes or, at the other extreme, from more purified mixtures containing primarily paclitaxel and cephalomannine is currently limited to the aforesaid non-economical chromatographic separation techniques and/or to non-selective oxidation methods, thereby presenting a serious and unfulfilled need for an economically practicable method for separating the valuable anti-tumor compound paclitaxel from its close analog cephalomannine, as well as other closely related taxanes.

It is therefore an object of this invention to provide a simpler and more cost effective method than currently available methods for the economical isolation and purification of the important chemotherapeutic compound paclitaxel.

SUMMARY OF THE INVENTION

To accomplish the aforementioned object, the present invention now provides a new and unique process for the isolation and purification of paclitaxel from crude biomass extracts containing a complex mixture of taxane type compounds inclusive of paclitaxel, and especially from the raw bark of *T. brevifolia*, *T. baccata*, *T. yunnanensis* and *T. walilichiana*, as well as from plant material such as needles and twigs from various taxus species and further including the downstream purification of paclitaxel produced from sources such as cell culture of taxus species and paclitaxel producing fungi.

Thus, in one aspect, the instant invention provides a process for the isolation and purification of paclitaxel from organic material containing, inter alia, a mixture of taxanes, which comprises solvent extraction of the organic material to form a paclitaxel-comprising composition, then chromatographically separating paclitaxel and other taxanes from the composition with a chromatographic solvent. This is preferably followed by a step of flash chromatographic separation of paclitaxel and other taxanes on a normal phase chromatographic column containing silica gel as an absorbent to form a refined mixture comprising paclitaxel, cephalomannine and other taxanes. The resulting mixture is then reacted with a halogen, preferably bromine, under conditions effective for the selective halogenation of the unsaturated side chain moiety of cephalomannine to produce a diastereomeric mixture of dihalocephalomannines; paclitaxel is then easily and conveniently separated from the mixture in high yield.

In another aspect of the invention, any step in the process for isolation and purification of paclitaxel from crude organic matter may be accompanied by the step of selective halogenation of cephalomannine, before or after extraction and purification by conventional chromatographic techniques, for example, notwithstanding whether the mixture is of a crude extract or of a more refined mixture of essentially all paclitaxel, cephalomannine and other taxanes.

In yet another aspect of the invention, there is provided a highly efficient and economical method for separating paclitaxel in virtually quantitative yield from its close analog cephallomannine by a novel chemical modification of cephalomannine.

The present invention is more fully understood by reference to the following detailed description of preferred embodiments of the invention, examples and drawings.

DETAILED DISCUSSION OF PREFERRED EMBODIMENTS

Figure 1:
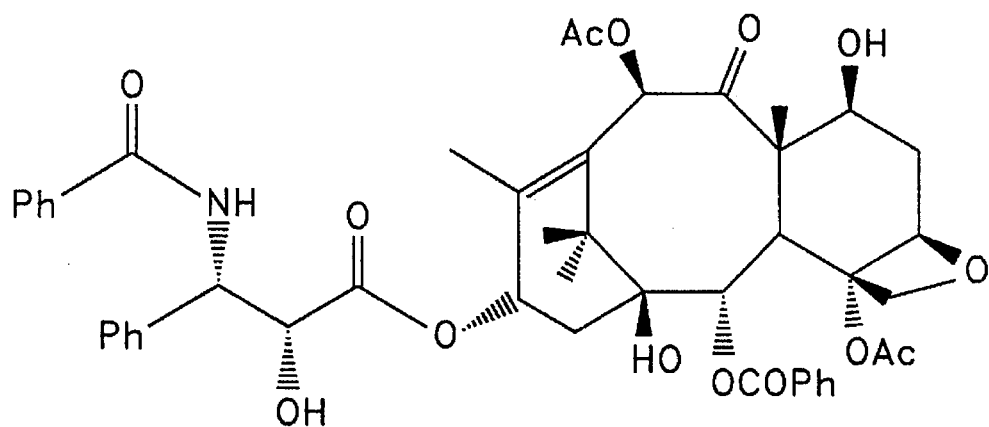
FIG. 1 illustrates a generalized representation of the structures of paclitaxel and cephalomannine.
Figure 1:
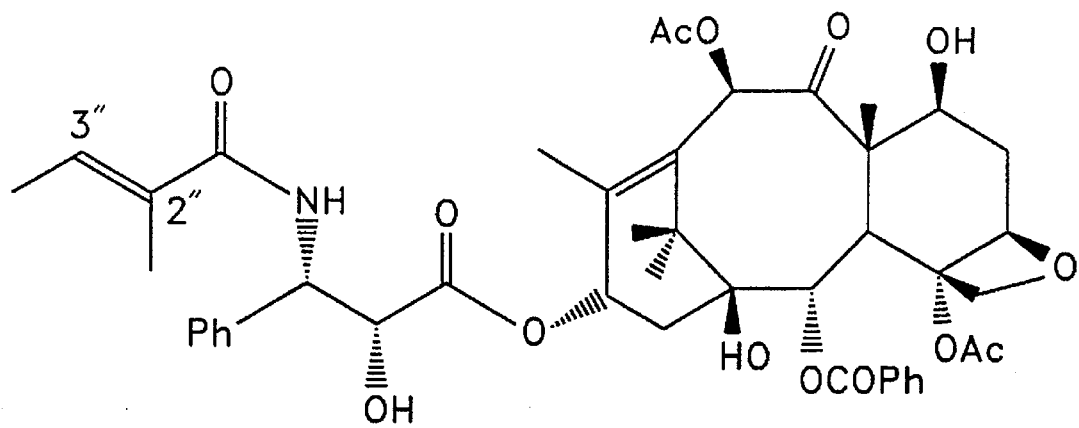

In the present inventive process, there is provided a simple and economic procedure for extracting purified paclitaxel from various sources of biomass, such as plant material containing a mixture of taxanes, for example, from the bark of *T. brevifolia* (Pacific Yew tree), *T. yunnanensis*, from needles and twigs of other Taxus species and from other sources of paclitaxel such as produced from cell cultures of the Taxus species and paclitaxel producing fungi.

The process comprises the selective halogenation, preferably bromination, of unpurified, partly purified, or purified mixtures of paclitaxel, cephallomannine and other taxane derivitives which contain unsaturated side chains to selectively transform certain taxanes without destroying paclitaxel.

In one embodiment of this process, biomass containing a complex mixture of various taxanes, if such is the case, is preferably processed to a high surface area to volume ratio of media to increase mass transfer of paclitaxel during an initial extraction phase, preferably with a lower alcohol, such as methanol, ethanol, etc. For example, using the bark of *T. brevifolia* as a source in which the concentration of paclitaxel is typically less than 0.1% w/w, the bark is ground to a fine mixture then extracted with methanol for a time deemed sufficient such that substantially all of the paclitaxel in the sample is extracted. The methanol extract is then concentrated, for example, by rotary evaporator, to preferably concentrate about twenty fold less in volume than the original extract.

Further extraction can be carried out, for example, by partitioning of the methanol concentrate between a suitable solvent such as methylene chloride, chloroform or ethylene dichloride and water, preferably in a 1:1 v/v ratio, in which water soluble components are extracted into the aqueous phase. Such components may be, for example, water-soluble glycosides of paclitaxel and other more polar compounds of the mixture which can be saved for additional processing of potentially valuable components. In this embodiment, the paclitaxel-comprising organic solvent phase is evaporated to a paclitaxel-comprising residue, and can be further purified by sedimentating the impurities. For example, by dissolving the residue in acetone tarry non-polar impurities are precipitated out with the addition of an equal volume of hexanes, and then can be filtered out. The acetone-hexanes soluble filtrate is then concentrated and a residue is precipitated from fresh hexanes. The obtained precipitate is then dried under high vacuum (1 mm to 2 mm) at 40° C.

In this embodiment it is preferred that this residue is next dissolved in a minimal amount of chromatographic solvent, such as methylene chloride or ethylene dichloride, and then flash chromatographed over a silica gel column. In this embodiment, the mobile phase can be, for example, a mixture of acetone and methylene chloride or ethylene dichloride in a 1:9 to 3:7 v/v ratio. The first few fractions of the column contain low polar compounds, followed by fractions containing varying concentrations of paclitaxel and cephalomannine. After the fractions have eluted out of the column, the silica gel is washed, for example, with acetone and methanol and the eluent discarded.

Fractions containing paclitaxel and cephalomannine are next combined and evaporated to again form a paclitaxel-comprising residue. This residue is next preferably dissolved in a chlorinated solvent, such as carbon tetrachloride, methylene chloride, chloroform or ethylene dichloride, to form a solution in which various unsaturated taxanes are halogenated under conditions effective for the selective halogenation of the unsaturated side-chain double bond in cephalomannine (and other taxanes containing side-chain unsaturation) to produce a diastereomeric mixture of dihalocephalomannines in solution with paclitaxel and other side chain halogenated taxane compounds. Although all of the halogens are contemplated for use in this invention, bromine is preferred because of its high efficiency and low cost. Preferably all of the cephalomannine present is substantially completely converted to the diastereomeric mixture of dihalocephalomannines to provide for an easy separation of paclitaxel from the mixture.

The taxanes in the chlorinated solvent are also preferably brominated under conditions of darkness, with vigorous mixing, and at a temperature close to 0° C. The reaction rate is desirably slow such that the rate of hydrobromic acid production is limited and there is little or no hydrolysis of residues of paclitaxel. After chromatographic analysis, for example HPLC, to determine if all, or substantially all, of the cephalomannine present has been completely reacted, the addition of bromine is terminated, and the chlorinated solvent solution containing, inter alia, paclitaxel and dibromocephalomannine isomers is preferably washed, for example, first with a dilute solution of sodium sulfite followed by sodium bicarbonate, to remove and neutralize any bromine or hydrobromic acid formed during the reaction.

The organic layer is further washed with water and dried with anhydrous sodium sulfate and then evaporated to dryness and the solid residue dissolved in a small amount of solvent, for example, methylene chloride, and fractions containing dibromocephalomannine isomers can be chromatographically separated from fractions containing paclitaxel, for example, by column chromatography over a silica gel column, preferably with an acetone and ethylene dichloride mixture of 1:9 v/v. Eluted fractions containing paclitaxel based on TLC and HPLC analysis are combined, then evaporated to a dry solid residue, from which purified paclitaxel can be recovered by dissolving the solid in acetone and crystallizing out paclitaxel with hexanes. The crystals are filtered, washed and dried to a final product.

Figure 3A:
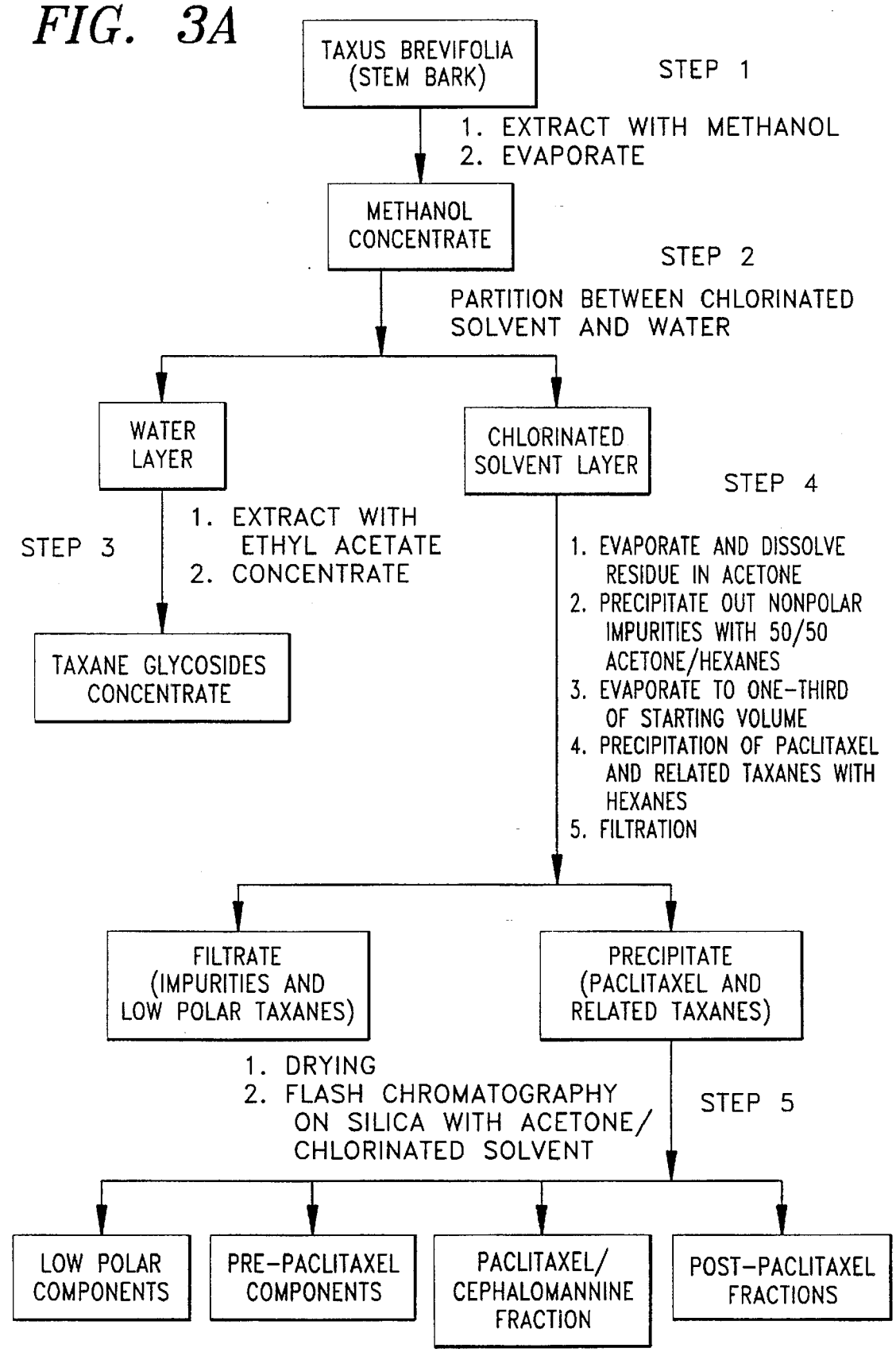
FIG. 3 is a flowchart of a preferred embodiment of one aspect of the invention in the isolation and purification of paclitaxel from *T. brevifolia*.
Figure 3B:
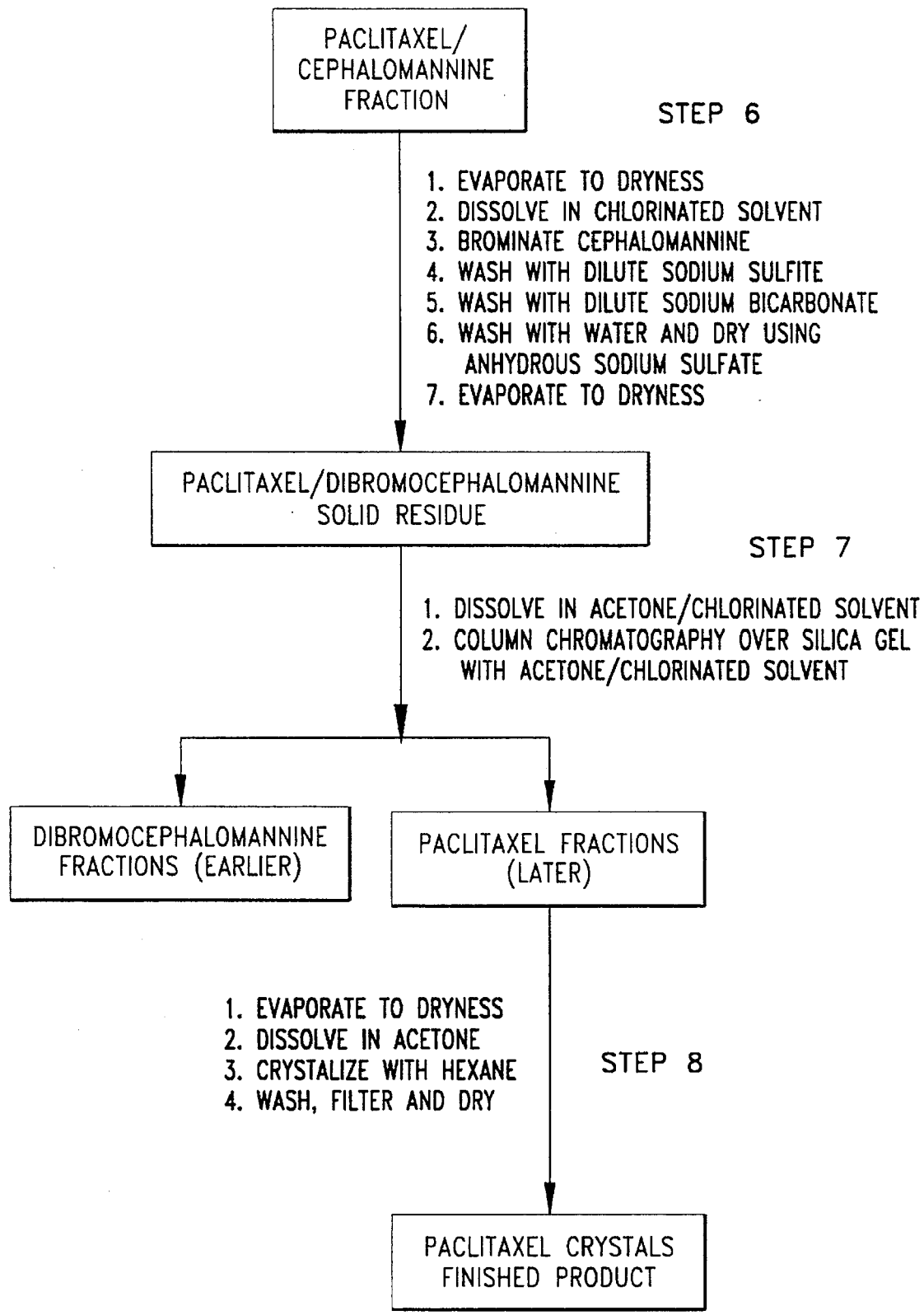
Figure 4:
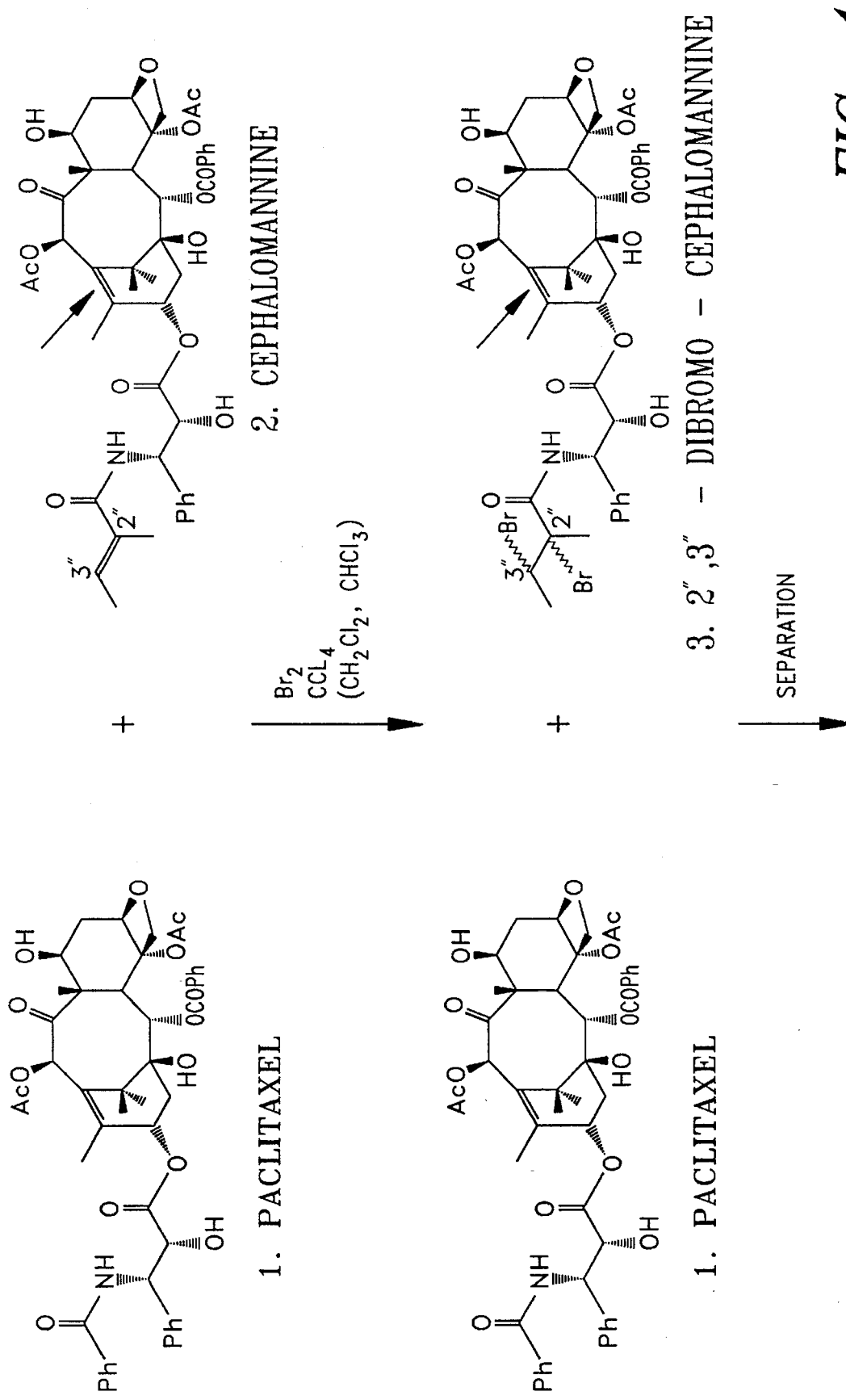
FIG. 4 illustrates a preferred reaction scheme for the selective bromination of cephalomannine.
Figure 5:
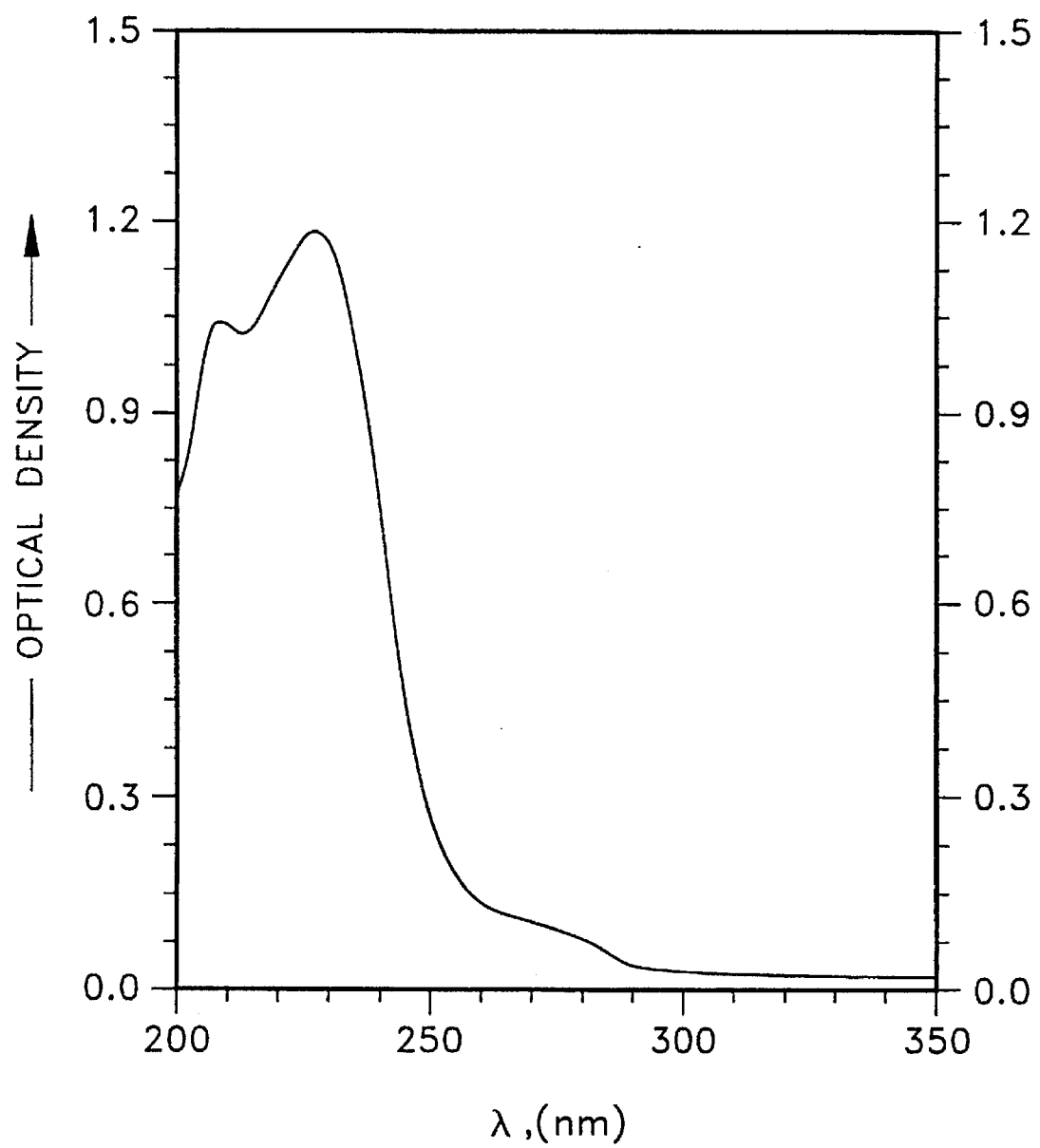
FIG. 5 is a UV spectrum of paclitaxel obtained from this invention.

The process is simple and easy to perform. Preferably, analysis of the product and by-product streams for paxlitaxel and cephalomannine are performed by HPLC and TLC such that any loss of product can be avoided. As shown, halogenation, particularly bromination, of cephalomannine is a novel and convenient way to increase the selectivity of paclitaxel during chromatographic separation of mixtures containing both paclitaxel and cephalomannine, and unlike various reported chemical modifications of taxanes the conditions for bromination can be controlled such that there is no significant loss of paclitaxel during the process. FIG. 3 illustrates a preferred process scheme for the isolation and purification of paclitaxel from $T.$ $brevifolla$, and FIG. 4 illustrates a preferred reaction scheme for the selective bromination of cephalomannine.

In accordance with this invention, the separation process is not dependent on the concentration of the paclitaxel present, nor on the compositions of the complex mixtures that are the starting points for the isolation and purification of paclitaxel. Therefore the present inventive procedure can conveniently be applied to the downstream isolation and purification of paclitaxel from other sources of paclitaxel such as cultured plant cells and paclitaxel producing fungi, with the step of selective halogenation contemplated for use in any step in the procedure to facilitate the isolation and purification of paclitaxel.

For mixtures containing cephalomannine and amounts of about 1% to about 99.9% paclitaxel, the halogenation process is similar to the one described above. The mixture is preferably dissolved in a large mount of chlorinated solvent, for example $CCl_4$, or $CHCl_3$ and after cooling close to 0° C. with stirring, a stoichiometric amount of bromine (1.2 molar equivalents relative to cephalomannine) diluted with $CCl_4$ or $CHCl_3$ is added until the cephalomannine is completely brominated. The entire reaction should be run in the dark at temperatures which should not exceed 20° C., preferably 5° C., and monitored, for example, by HPLC analysis. After the bromination is finished, the reaction mixture is washed to remove the excess bromine.

In all cases, the cephalomannine and other unsaturated taxanes are brominated with a high recovery of the paclitaxel. The resulting mixtures containing paclitaxel and brominated compounds are separated and purified using a variety of methods such as chromatography and crystallization. The transformation of the cephalomannine to the less polar dibromo derivative gives possibilities for an easier separation of paclitaxel from the mixture.

Figure 2:
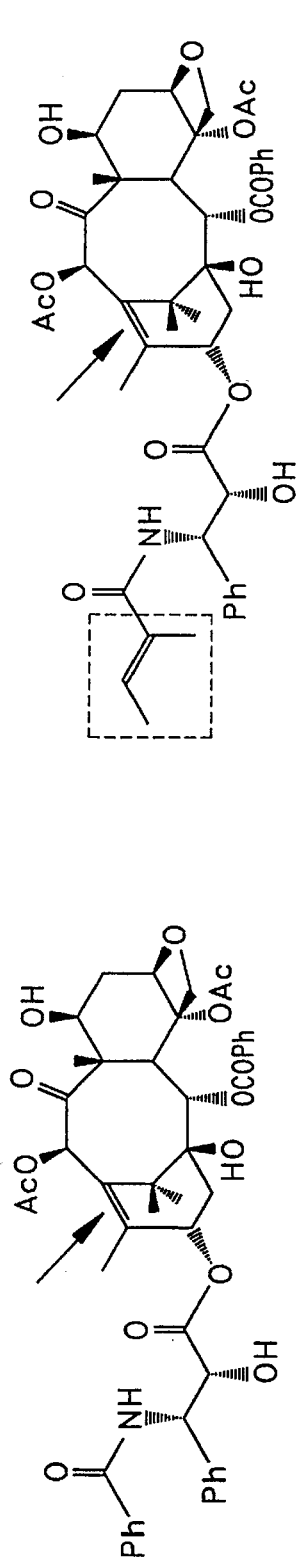
FIG. 2. illustrates a generalized representation of the structures of several unsaturated taxanes and functional groups contained therein with various unsaturated side chains, which can be halogenated in accordance with this invention.
Figure 2:
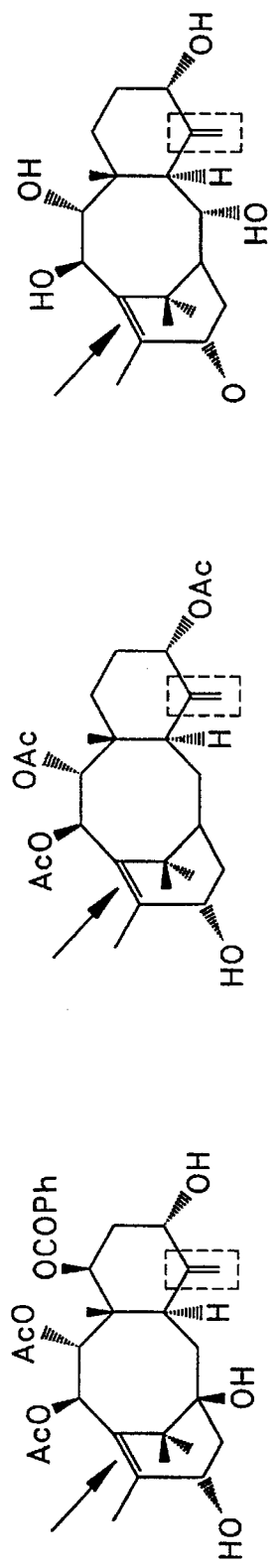
Figure 2:
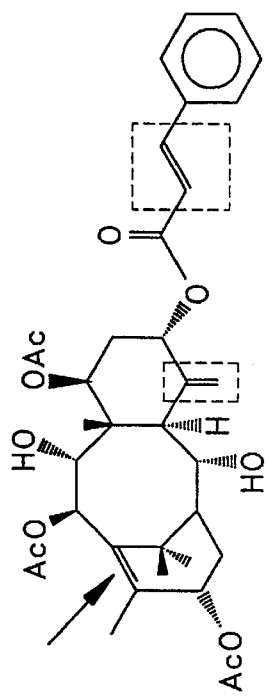
Figure 2:
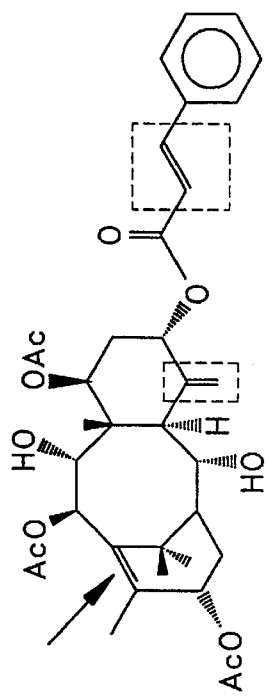
Figure 2:
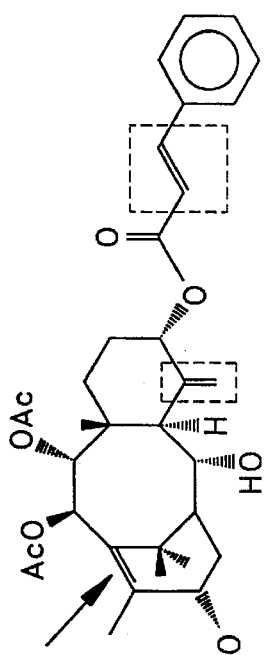

The number of molar equivalents of bromine added to the mixture depends mainly on the concentration of cephalomannine and the other unsaturated compounds. Generally, a less pure mixture (containing a high amount of unsaturated taxanes relative to cephalomannine) requires more molar equivalents of bromine to completely brominate the unsaturated taxanes than would a purer mixture. FIG. 2 illustrates the structures of various unsaturated taxanes. If the mixture has a high content of unsaturated compounds such as taxicin, taxicin-I, taxinin, brevifoliol the molar equivalents will be higher because they will absorb more than 1 molar equivalent of bromine.

Solvents that can be used for the process of halogenation must be inert to the halogen employed, especially the preferred bromine. Useful and preferred solvents in accordance with this invention are chlorinated solvents such as $CCl_4$, $CHCl_3$, $CH_2Cl_2$, $C_2H_4Cl_2$, with $CCl_4$ being most preferred. The halogenation process is most effective within the temperature range of about −20° C. to about +20° C., preferably from about −5° C. to about 5° C. with bromine. A preferred reagent for the above reactions is 0.01M to 0.1M bromine in carbon tetrachloride, or chloroform, which is commercially available.

Conventional wisdom would suggest that in using a halogen such as bromine to brominate taxane compounds containing several functional groups which are sensitive to bromine or other halogens, various unwanted reactions will occur with the paclitaxel or the other compounds listed in FIG. 2. However, instead, it has been found that selectivity for the side-chain double bond of cephalomannine is unexpectedly very high, as well as for the selective bromination of other taxanes containing exocyclic double bonds. In the process of this invention, paclitaxel is neither significantly degraded nor brominated during the reaction. Paclitaxel, however, may degrade to several unidentified compounds if the reaction is exposed to a large amount of light, or if a large excess of halogen is employed. Any degradation of paclitaxel during the halogenation (bromination) reaction can be easily avoided by periodically monitoring the reaction by HPLC.

EXAMPLES

The following examples are related to the purification of paclitaxel by a preferred embodiment of the inventive process. All chemicals were used as received from the manufacturer/supplier. The paclitaxel and cephalomannine resulting from all product and by-product streams were monitored by thin-layer chromatography using Merck #5554, $F_{254}$ Silica gel plates and by HPLC. The HPLC system consists of a Waters 510 pump, 660E system controller, 712 WISP or 710E WISP autoinjector, Waters 490 program multiwavelength detector, Waters 990 photodiode array detector and NEC APCIV computer and Waters LambdaMax model 481 spectrophotometer and data module. HPLC columns used include a 3.9 mm×300 mm phenyl reversed phase Waters μbondapak column and a phenyl guard column. Silica gel for flash chromatography was 32–63 mm mesh size supplied by ICN Biomedicals.

It it to be understood, however, that the following examples are for illustrative purposes only, and are not intended to limit the scope or the spirit of this invention or the claims in any way.

Example 1

Purification of Paclitaxel from Raw Biomass

Step 1

Bark from the Pacific yew, *Taxus brevifolia* is shredded to between 2 to 4 mm in size. The concentration of paclitaxel in the bark is between 0.03–0.1% w/w. 45 kg of the bark is fed into a stainless steel tank. This is extracted thrice with 150 liters of methanol. Each extraction is performed over a period of 5 days with frequent recirculation of the extract to promote mixing. The extract is concentrated by rotary evaporation to a concentrate between 10–15 liters in volume. The temperature of the extract did not exceed 40° C. Nearly 99% of the paclitaxel is extracted into the methanol phase by this method.

Step 2

The methanol concentrate from step 1 is partitioned, for example, between methylene chloride, or ethylene dichloride and the like, and water. To 15 liters of the methanol extract, equal volumes of methylene chloride and water are added. The mixture is stirred slowly for 15 minutes and allowed to stand for a period of 2 hours. The two phases are separated. The methylene chloride phase is further processed for isolation of paclitaxel. If upon analysis, paclitaxel remains in the aqueous phase it is then reextracted with methylene chloride and the methylene chloride fraction is pooled with the same fraction from the first extraction. Methanol (0.5–1 liters) is added to the mixture if emulsions are formed during mixing and are required to be broken. The methylene chloride extract is rotary evaporated to dryness. The solid residue is between 0.9–1.1 kg containing 1.8–2.2% w/w of paclitaxel. The temperature of the product during processing are not allowed to exceed 40° C.

Step 3

The aqueous fraction from step 2 contains glycosides of paclitaxel, 10-deacetyl baccatin III, baccatin III and other polar compounds. To 35 liters of the aqueous fraction, 5 liters of brine solution is added. This is extracted with 20 liters of ethyl acetate. The two phases are separated. The upper, ethyl acetate layer contains glycosides of paclitaxel, 10-deacetyl baccatin III, baccatin III and other polar compounds. The lower, aqueous phase is reextracted with ethyl acetate and the ethyl acetate fraction is pooled with the same fraction from the earlier extraction. The pooled ethyl acetate fraction, which is between 30–35 liters, is then concentrated by rotary evaporation to a viscous dark brown solution between 2.8–3.2 liters. This is stored for further processing to isolate glycosides.

Step 4

The methylene chloride solid residue from step 2 is dissolved in 2 liters of acetone. An equal volume of hexanes is added under conditions of intensive agitation. Polar impurities are precipitated out under these conditions. They are allowed to settle and the supernatant is decanted for further processing. The precipitate is washed with acetone/hexanes (1/1 v/v) and the flitrate is pooled with the previous supernatant. The supernatant is evaporated to one-third (⅓) volume by rotary evaporation. The viscous residue is between 1.5 L–3.0 L and is yellowish brown in color.

Step 5

The acetone/hexanes residue from step 4 is added dropwise to 10~15 L hexanes, while stirring vigorously. A light yellow material starts precipitating. After approximately 8 hours this material is filtered and dried under high vacuum (1 mm to 2 mm) at 40° C. to yield about 0.5~0.6 kg material.

Step 6

The solid residue from step 5 is next dissolved in 0.5 liters of an acetone-methylene chloride, 1:9 v/v mixture, and flash chromatographed over a silica gel column using the same solvent as the mobile phase. The amount of silica gel used is between 3.5–4 kg. The fractions were collected in volumes of 1 liter. Each sample was analyzed by TLC and HPLC. Cephalomannine co-eluted out with the paclitaxel. The fractions containing paclitaxel and cephalomannine are pooled together and rotary evaporated to dryness. The solid residue is a crude mixture of paclitaxel and cephalomannine of between 55 gm to 70 gm containing 45–55% w/w of paclitaxel, or about 36 g–40 g paclitaxel.

Step 7

A crude mixture of paclitaxel and cephalomannine from Step 6 found to contain 28.8% w/w of cephalomannine and 51.2% w/w paclitaxel after analysis, is next chemically modified to separate the paclitaxel from the cephalomannine. 10 g of the crude mixture is dissolved in 1 liter of a chlorinated solvent, such as, for example, carbon tetrachloride, chloroform, methylene chloride or ethylene dichloride. In this preferred embodiment, a 0.01M solution of bromine in carbon tetrachloride is reacted very slowly with the crude solution under conditions of darkness and at a temperature of 0° C. with vigorous mixing. Reaction progress is monitored by HPLC. The bromination reaction is terminated when the cephalomannine has been completely reacted. Trace amounts of bromine are removed by washing with an aqueous solution of sodium sulfite. Hydrobromic acid formed during the reaction is washed off with a dilute sodium bicarbonate solution (0.5%) w/w). The resulting organic extract is then dried with anhydrous sodium sulfate and concentrated on a rotary evaporator to a solid residue which is 13.2 g by weight.

Step 8

The brominated residue from step 7 is dissolved in an acetone/methylene chloride mixture, 1:9 v/v, and chromatographically separated over a silica column. The fractions collected were analyzed by TLC and HPLC. The paclitaxel-containing fractions were pooled together and evaporated to dryness by rotary evaporation. The solid residue is white and has a mass of 6.1 g.

Step 9

The solid residue from Step 8 was next dissolved in acetone and crystallized with an equal volume of n-hexane or hexanes. The crystals were washed with cold acetone/hexane, 1/1 v/v, solution and then dried under vacuum at 40° C. The solid crystals weighed 4.84 g and contained >97% w/w of paclitaxel as measured by HPLC.

Example 2

Bromination of Partially Purified Cephalomannine

A solution of 0.63 g 91.5% cephalomannine (0.0007 moles) containing about 6–7% paclitaxel dissolved in 150 mL carbon tetrachloride was added to a 500 mL three neck round bottom flask, fitted with a 250 mL separatory funnel. The flask was immersed in an ice-salt bath. When the temperature reached –5° C., a solution of bromine (0.1221 g) in carbon tetrachloride (76.31 mL, 0.01M) was added slowly with stirring at such a rate that the reaction temperature did not exceed 5° C. The cephalomannine to bromine ratio was 1:1.1 mole. The addition required about three hours and the resulting solution was light brown and cloudy.

The bromination was monitored by HPLC analysis every hour. The reaction is complete when all the cephalomannine present is converted to the 2",3"-dibromo-derivative, which based on HPLC, required approximately 8 hrs. The reaction mixture was light yellow to colorless, due to the consumption of the bromine.

The reaction mixture was next transferred to a one liter separatory funnel and first washed with 0.5% aqueous sodium sulfite (300 mL), 0.5% aqueous sodium bicarbonate (300 mL) and then twice with deionized water (200 mL each) to a final pH 6.5. The combined aqueous layer was extracted once with $CH_2Cl_2$ and the $CH_2Cl_2$ layer mixed with the previous organic extract. It was then dried over $Na_2SO_4$, filtered, and evaporated to dryness. The yield was 0.76 g of a light cream-colored solid which is approximately a 100% yield based on the starting material.

The cream colored solid material was chromatographed on a column of silica gel (50 g, ICN Silitech, 32-63 D, 60 A) using acetone/$CH_2Cl_2$ (10:90) as the eluent. Fifty ml fractions were collected and checked by TLC (Silicagel 60 $F_{254}$, Merck #5554, developed with acetone/$CH_2Cl_2$ (20/80), and detected using vanillin-sulfuric acid in methanol spray reagent). The fractions with a single spot at $R_f$=0.64 (fractions #26–#38) were mixed, concentrated to dryness to yield 0.485 g of a light cream to white crystalline solid, mp: 158° C., identified as 2",3"-dibromocephalomannine. The yield was estimated to be 70% on the basis of starting cephalomannine.

Example 3

Bromination of a Crude Mixture Containing Cephalomannine, Paclitaxel and Other Taxane-type Compounds Using similar apparatus as used in Example 2, a sample of crude paclitaxel (2.0 g) of a mixture of 51.2% paclitaxel 28.8% cephalomannine, and about 20% other taxanes or non-taxane impurities based on HPLC was dissolved in 150 mL carbon tetrachloride and 150 mL $CH_2Cl_2$, to yield a clear, light yellow solution. The flask was immersed in an ice-salt bath and stirred. When the temperature reached –5° C., a solution of 0.1332 g 100% bromine in 83.13 mL (0.01M) of carbon tetrachloride (1M cephalomannine:1.2M bromine) was added to the solution at such a rate that the temperature of the reaction mixture did not exceed 5° C. The addition required about three hours and resulted in a cloudy, brownish-yellow solution. After the addition of bromine was completed, the reaction was allowed to continue under the same conditions for an additional 8 hours, with HPLC analyses of the paclitaxel and cephalomannine performed every hour. The reaction is complete when the solution is colorless or light yellow and all the cephalomannine has been converted to the dibromo derivative. If after the additional 8 hours the solution still contains more than 1–2% cephalomannine, keeping the initial conditions, 10 mL 0.01M bromine in carbon tetrachloride were added dropwise and allowed to react for 1 hour before again analyzing with HPLC.

Excess bromine from the reaction mixture was removed by washing with 0.5% aqueous $Na_2SO_3$ (300 mL), 0.5% aqueous $NaHCO_3$ (200 mL), and deionized water (2×200 mL). The reaction mixture was dried using anhydrous $Na_2SO_4$ and concentrated to dryness under high vacuum to yield 2.35 g of dry light cream to white crystalline residue. The dry material was then purified on a silica gel column under the conditions listed in Example 2. The ratio between the mixture to be separated and the silica gel was 1:60, thus 120 g silica gel were used. Each fraction was checked by TLC and every third fraction by HPLC. Fractions with the same $R_f$ in TLC and same retention time in HPLC were mixed to afford two combined fractions. Fractions (#25–#39) which showed a single TLC spot with $R_f$ 0.64 represented dibromo-cephalomannine and fractions (#41–#81) which showed a single TLC spot with $R_f$ 0.49 represented paclitaxel.

Fractions #25–#39 on concentration to dryness at ca 40° C. under high vacuum yielded a white to light yellow solid (0.460 g, 66.6% theoretical yield).

Analysis of the obtained dibromocephalomannine is as follows:

m.p. 158°–160° C. (chromatographic purity 96.19%)

$R_f$=0.64 (single spot) on Silica gel 60 $F_{254}$ Plate (Merck, #5554)

Solvent system:acetone:$CH_2Cl_2$ (20:80)

Spray Reagent:Vanillin/Sulfuric Acid in Methanol

Mass Spectrum [FAB]$^+$:
  $[M+H]^+$=990, 992, 994
  $[M+Na]^+$=1014
  $[M+K]^+$=1030

Concentration of the second combined fractions (#41–#81) yielded 1.16 g (>100% theoretical yield) paclitaxel, which was recrystallized using 50:50 acetone/hexane, filtered, washed with the same ratio of cooled solvent and dried under high vacuum at 40° C. for 24 hrs. The yield was 0.902 g (45.11% theoretical based on the weight of the starting material or 88.1% based on the HPLC analysis of paclitaxel in the starting material) of a white crystalline material.

Analysis of the separated and purified paclitaxel is as follows:

m.p. 214°–216° C.

$R_f$=0.49 in the presence of authentic sample on silica gel 60 $F_{254}$ plate [Merck #5554]

Solvent system: Acetone/$CH_2Cl_2$ (20:80)

Spray Reagent: Vanillin/Sulfuric Acid in Methanol

UV Spectrum in $CH_3OH$: 228.4 (297146.8) ($\lambda_{max}$ in nm, ($\epsilon$)) 206.6 (26540.1)

IR spectrum in KBr (cm$^{-1}$) 3500, 1105, 1070 (tert & sec. OH) 3430, 1650, 1580 (—CONH—) 3070, 1610, 1520, 780, 710 (monosub. aromatic rings) 2950, 2910, 1480, 1450), 1370 ($CH_3$, $CH_2$, CH) 3020, 1315, 980 (double bond) 1730, 1270 (aromatic esters) 1715, 1240 (>C=O) 1730, 1180 (acetates) 850 (epoxy ring)

Both the UV and the IR spectra match those of pure paclitaxel.

Example 4

Separation and Purification of Paclitaxel from a Crude Mixture of Taxanes, and Analysis Thereof A solution of 10.00 g crude paclitaxel (on the basis of HPLC analysis the content was 28.8% cephalomannine, 51.2% paclitaxel and approximately 20% other taxane or non-taxane impurities) was dissolved in 1.5 L carbon tetrachloride in a 2.0 L three-necked flask fitted with a 500 mL separatory funnel, reflux condenser, thermometer and magnetic stirrer and immersed in an ice-salt bath. The reaction mixture was stirred until the temperature reached –5° C. and then 41.2 mL of 0.1M bromine (0.665 g bromine) in carbon tetrachloride was added dropwise for about 3 hours. The molar The ratio between cephalomannine and bromine was 1:12. The reaction temperature did not exceed 5° C. After the bromine addition was completed, stirring was continued while maintaining the temperature at –1° to 5° C. The reaction was monitored by HPLC every hour until all the cephalomannine had been converted to the dibromo derivatives (approximately 8 hrs.). The final color of the 1500–1600 mL of solution was light yellow or cream, depending on the color of the starting mixture and the possible presence of a small excess of bromine.

To remove any trace of bromine, the reaction mixture was washed with 0.5% aqueous $Na_2SO_3$ (500 mL), 0.5% aqueous $NaHCO_3$ (500 mL), and deionized water (2×500 mL). The reaction mixture was dried with anhydrous $Na_2SO_4$, and concentrated to dryness under vacuum to yield 13.20 g of a light cream to white crystalline material.

This material was chromatographically separated on a silica gel column under the conditions listed above in Examples 2 and 3. A 100×5 cm glass column was prepared by the slurry method with 600 g silica gel (ratio 1:50). The column was eluted with acetone/$CH_2Cl_2$ (10:90). A 1 L acetone/$CH_2Cl_2$ (25:75) was used as a final column wash. Every fraction was analyzed by TLC and every third fraction by HPLC. Fractions #11–#22 showed a single spot at $R_f$=0.64 and after combination, concentration and drying on a Buchi rotavapor (40° C. high vacuum), yielded 3.25 g (95%) of 2",3"-dibromocephalomannine as a white to light yellow solid.

Analysis of the product is as follows:

m.p.: 158°–160° C.

$R_f$=0.64 (single spot) on silica gel 60 $F_{254}$ plate [Merck #5554].

Solvent system: Acetone/$CH_2Cl_2$ (20:80)

Spray Reagent: Vanillin/Sulfuric Acid in Methanol.

Elemental Composition and Molecular Weight (on the basis of HR FAB$^+$)

$C_{45}H_{54}NO_{14}{}^{79}Br_2$ $[M+H]^+$: Calculated: 990.191000 Found: 990.191103 ($\Delta m$=0.1 ppm)

$C_{45}H_{54}NO_{14}{}^{79}Br^{81}Br$ $[M+H]^+$: Calculated: 992.181000 Found: 992.189057 ($\Delta m$=8.1 ppm)

$C_{45}H_{54}NO_{14}{}^{81}Br_2$ $[M+H]^+$: Calculated: 994.175000 Found: 994.187011 ($\Delta m$=12.1 ppm)

$C_{45}H_{53}NO_{14}Na^{79}Br^{81}Br$ $[M+Na]^+$: Calculated: 1014.161000 Found: 1014.171002 [$\Delta m$=9.9 ppm]

$C_{45}H_{53}NO_{14}K^{79}Br^{81}Br$ $[M+K]^+$: Calculated: 1030.097000 Found: 1030.144940 [$\Delta m$=46.5 ppm]

UV Spectrum in $CH_3OH$: 274.2 (1550.8); 227.1 (18610.4); 221.8 (18325.1) [$\lambda_{max}$ nm, ($\epsilon$)]

IR Spectrum in KBr (cm$^{-1}$) 3500, 1105, 1070 (tert & sec OH) 3420, 1670, 1580, (—CONH—) 3110, 3060, 1605, 1505, 770, 710 (monosubt. aromatic cpds.) 3060, 2960, 2915, 2870, 1465, 1370 (—$CH_3$, —$CH_2$—, =CH—) 3020, 1670, 1310, 980 (double bond) 1730, 1270 (aromatic esters) 1715, 1240 (>C=O) 1730, 1180 (acetates) 855 (epoxy tings) 520 (bromo compounds)

| $^1$H NMR in $CDCl_3$ (300 MHz): | 1.94 (d, 3H, —COC(Br)$\underline{CH_3}$ -5") |
|---|---|
| (ppm; side chain protons only) | 1.98 (d, 3H, —HC(Br)$\underline{CH_3}$ -4") |
| | 4.63 (qt, 1H, —$\overset{\shortmid}{\underline{CH}}$(Br) -3") |
| $^{13}$C NMR (300 MHz) | 170.21 and 170.25 (C-1') |
| (in ppm; side-chain C only) | 172.26 and 172.32 (C-1") |
| | 72.76 and 72.90 (C-2') |
| | 69.71 and 69.88 (C-2") |
| | 54.34 and 54.52 (C-3') |
| | 55.13 and 55.35 (C-3") |
| | 30.39 and 30.77 (C-4") |

| | | |
|---|---|---|
| | 27.21 and 27.62 (C-5") | |
| EIMS: [M]⁺ | 568, 551, 509 491, 449, 431, 405, 391, 386, 329, 326, 308, 278 | |
| (m/z) (the main fragments) | 264, 245, 217, 200, 188, 159, 149, 122, 105, 91, 83, 77, 55, 43. | |
| DCIMS: [M + H]⁺ | 569, 552, 510, 492, 474, 450, 432, 424, 392, 387, 370, 329, 327, | |
| (m/z) (the main fragments) | 309, 279, 265, 264, 246, 218, 200, 188, 167, 149, 125, 124, 106, | |
| | 101, 100, 91, 83, 69. | |
| FAB⁺ – MS: | 1030[M + K]⁺; 1014[M + Na]⁺; 992[M + H]⁺ (See Elem. Anal.); | |
| (m/z) | 974[M – $H_2O$]⁺; 932[M – AcOH]⁺; 914[M – AcOH – $H_2O$]⁺; | |
| | 912[M – HBr]⁺; 870[M – BzOH]⁺; 854[870 – $H_2O$ – 2H]; | |
| | 832[M – 2HBr]⁺; 705[M-243 – Ac]⁺; 569[T]⁺; 551[T – $H_2O$]; | |
| | 509[T – AcOH]⁺; 491[T – AcOH – $H_2O$]⁺; 448[T – BzOH]⁺; | |
| | 429; 424[$SH_2$]⁺; 413; 405[S – $H_2O$]⁺; 391[S – O – $H_2O$]⁺; | |
| | 387[T – AcOH – BzOH]⁺; 376; 347[S – O – CO—HCHO]⁺; 338: | |
| | 327[387 – AcOH]⁺; 315; 284[327 – Ac]⁺; 279; 264[832 – T]⁺ or | |
| | [424 – 2HBr]⁺; 246[264 – $H_2O$]⁺; 231; 218[264 – HCOOH]⁺; 188; | |
| | 167[S – $C_5H_8ONBr_2$]⁺; 149[167 – $H_2O$]⁺; 133; 122[BzOH]⁺; 113: | |
| | 105[Bz]⁺; 91[$C_7H_7$]⁺; 83; 77[$C_6H_5$]⁺; 76; 57; 55; | |
| | (T = taxane ring in the compound; S — acid (side) chain in the | |
| | compound.) | |
| HPLC: | | |
| Condition 1: | Column | CN 10µ (250 × 4.6 mm) |
| | Solvent System | $CH_3CN:H_2O$ (40:60) |
| | Flow Rate | 1 mL/min |
| | Detector | Waters 490 at 227 nm |
| | Injection volume | 20 µL |
| | $RT_{2",3" - dibromocephalomannine}$ | 26.06 min. |
| Condition 2: | Column: | Curosil G 6µ (250 × 3.2 mm) |
| | Solvent System | $CH_3CN:H_2O$ (45:55) |
| | Flow Rate | 0.75 mL/min |
| | Detector | Waters 490 at 227 nm |
| | Injection Volume | 20 µL |
| | $RT_{2",3" - dibromocephalomannine}$ | 2 diastereomeric forms: |
| | | $RT_I$ = 23.53 |
| | | $RT_{II}$ = 24.50 |
| Thermogravimetric Analysis (TGA): | Temperature (Stability %): 28.04° C. (100.0%), 100.00° C. | |
| | (99.64%), 150.00° C. (98.88%), 175.00° C. (95.35%), | |
| | 180.00° C. (86.74%), 200.00° C. (60.38%), 250.00° C. | |
| | (45.30%). | |
| Differential Scanning Calorimetry (DSC): | 173.76° C., 187.73° C. | |

The fractions from #26 to #68 which had a singlespot in TLC ($R_f$ 0.49, the same as the authentic sample of paclitaxel) and a single peak in the HPLC were combined, concentrated and dried on a Buchi rotavapor (40° C. high vacuum) to yield 6.10 g of a white solid. This material was crystallized from 60 ml of a mixture of acetone/hexane mixture (50:50), filtered, washed with the same ratio of cooled solvents and dried under high vacuum at 40° C. (24 hrs.) to obtain 4.84 g (92%) of a white crystalline solid identified by comparison to an authentic sample as paclitaxel.

Analysis of the purified paclitaxel is as follows:
  m.p.: 214° C.–216° C.
  TLC: $R_f$: 0.49 (in the presence of the authentic sample)
    Silica gel 60 $F_{254}$ plate (merck #5554)
  Solvent system: acetone/$CH_2Cl_2$ (20:80)
  Spray Reagent: Vanilin/Sulfuric Acid in Methanol

| | Elemental Analysis: | | |
|---|---|---|---|
| $C_{47}H_{51}O_{14}N$: | % C | % H | % N |
| Calculated | 66.11 | 6.02 | 1.64 |
| Found | 65.97 | 5.89 | 1.63 |

FIG. 5

Figure 6:
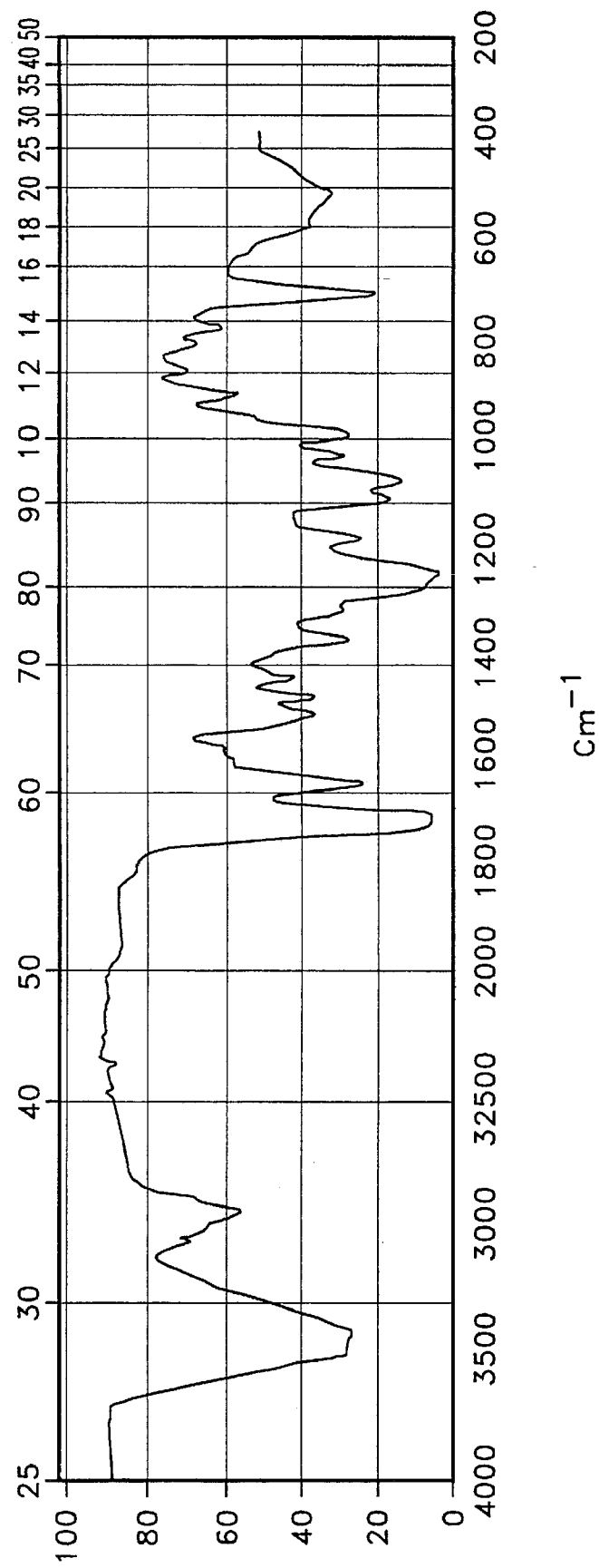
FIG. 6 is an IR spectrum of paclitaxel obtained from this invention.
Figure 7A:
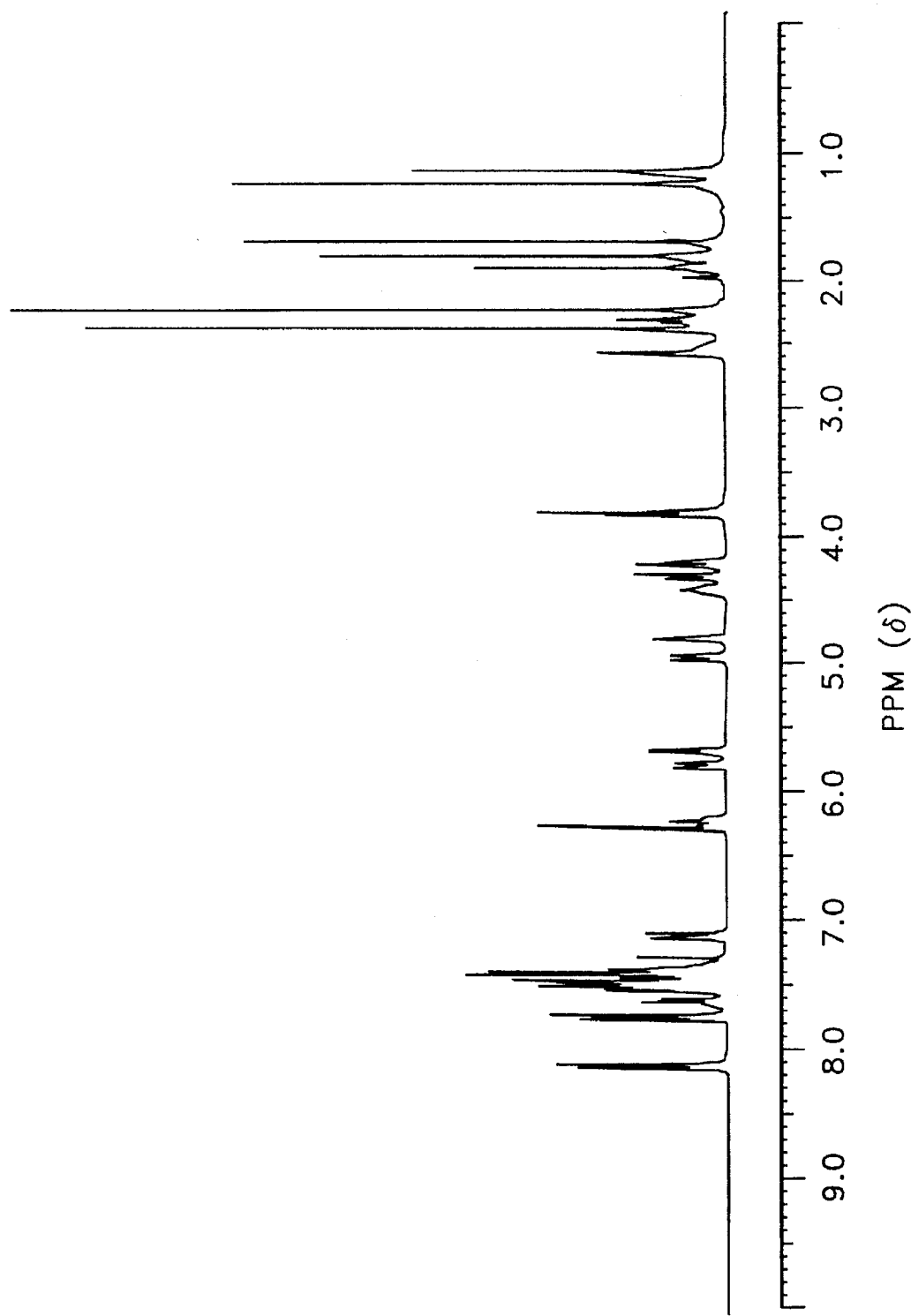
FIG. 7a is a proton NMR spectrum of paclitaxel obtained from this invention.

| | |
|---|---|
| UV Spectrum in $CH_3OH$: | 227.2 (29824.1) |
| ($\lambda_{max}$ in nm, ($\epsilon$)) | 208.0 (26256.3) |
| FIG. 6 | |
| IR Spectrum (KBr) (cm⁻¹) | 3500, 1105, 1070 (tert. & sec. OH) |
| | 3430, 1650, 1580 (—CONH—) |
| | 1610, 1520, 780, 710 (monosub. aromatic rings) |
| | 2950, 2910, 1480, 1450, 1370 (—$CH_3$, —$CH_2$—, >CH— groups) |
| | 3020, 1315, 980 (double bond) |
| | 1725, 1270 (aromatic esters) |
| | 1710, 1240 (>C=O) |
| | 850 (epoxy rings) |
| FIG. 7a | |
| ¹H NMR Spectrum | 1.88(S, 1 OH, C-1); 5.66(d, 1H, C-2); 3.82(dd, 1H, C-3); |

Figure 7B:
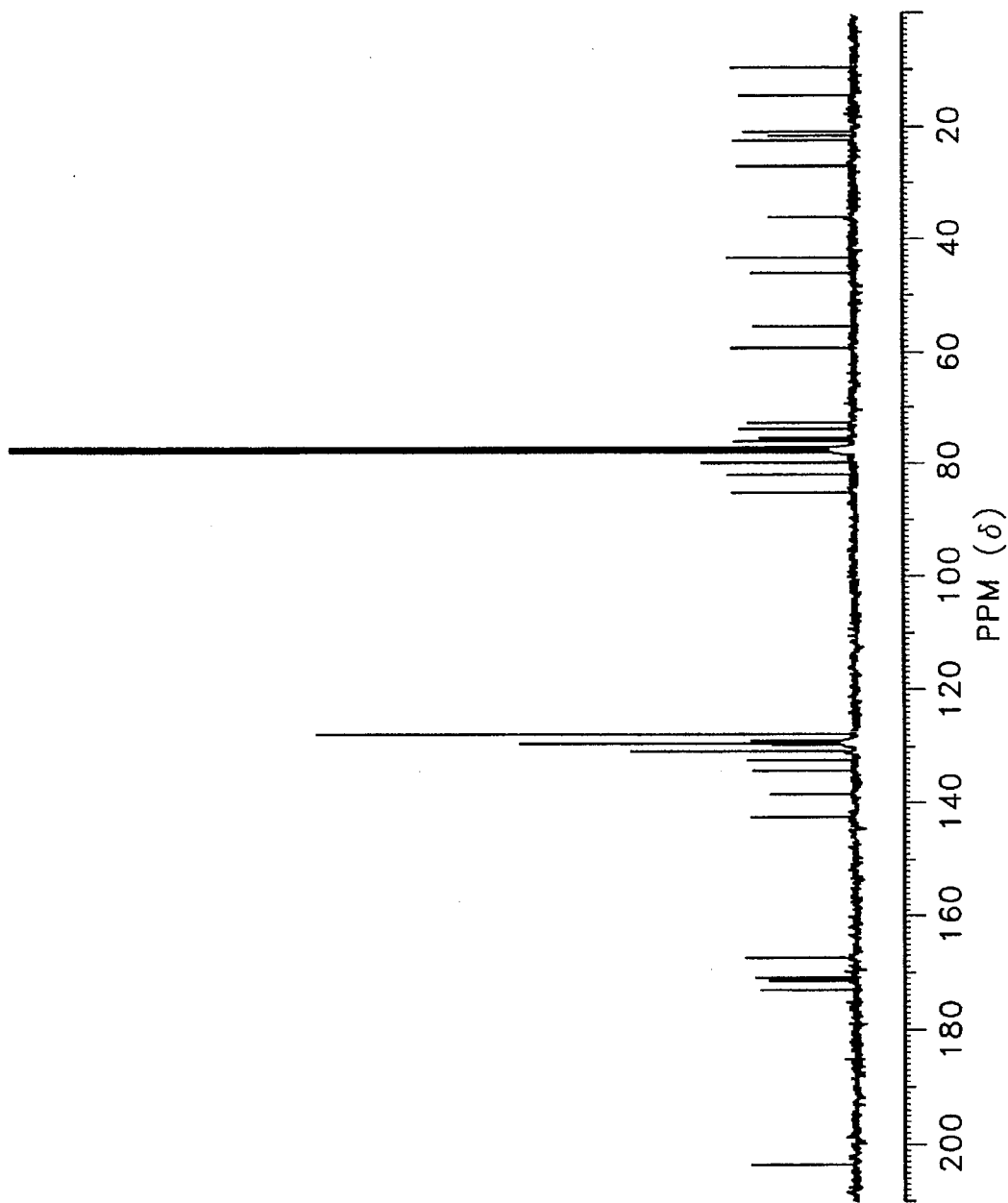
FIG. 7b is a carbon-13 NMR spectrum of paclitaxel obtained from this invention.
Figures 8A, 8B:
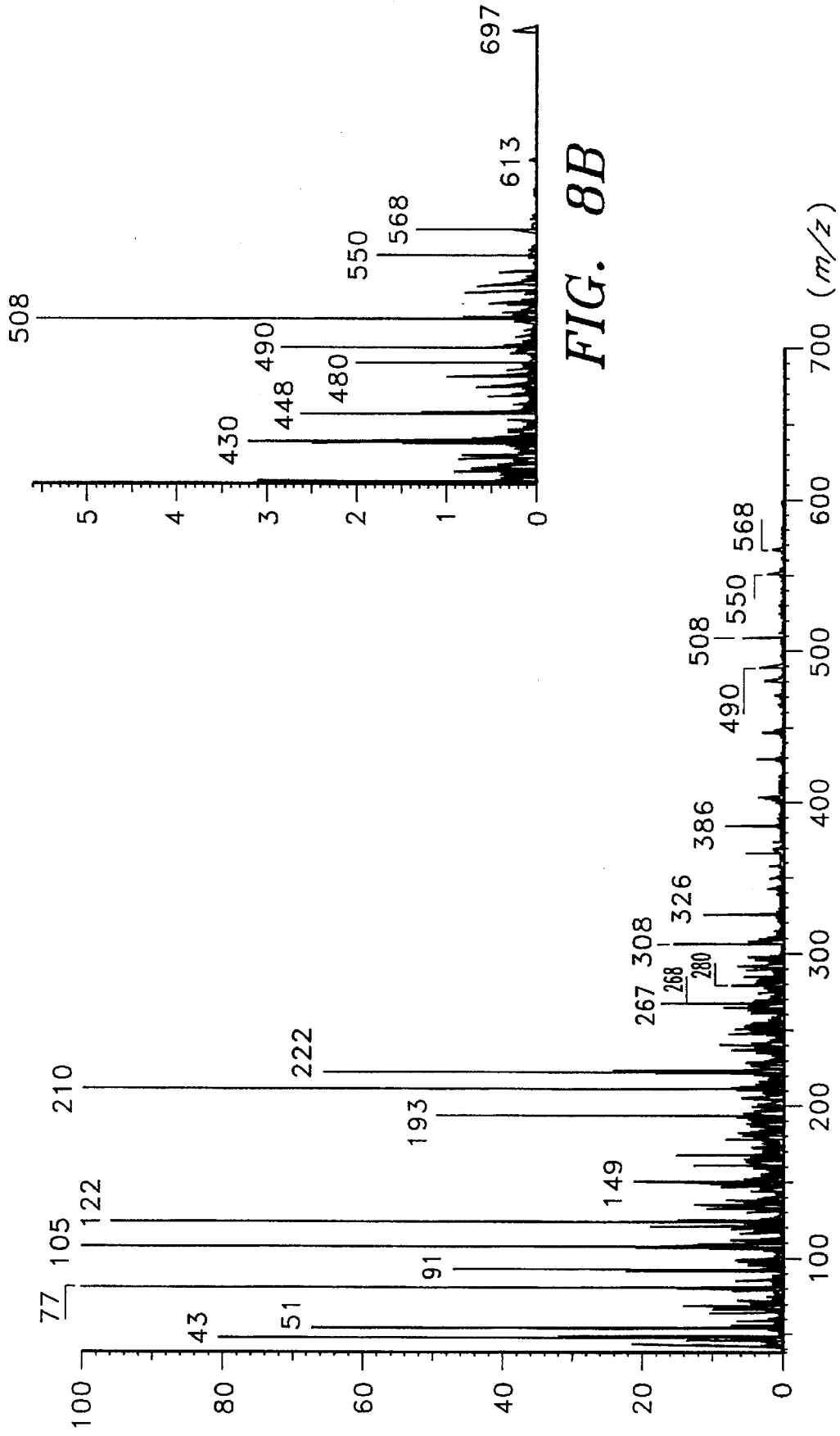
FIGS. 8a and 8b are EI-MS of paxlitaxel obtained from this invention.
Figure 9:
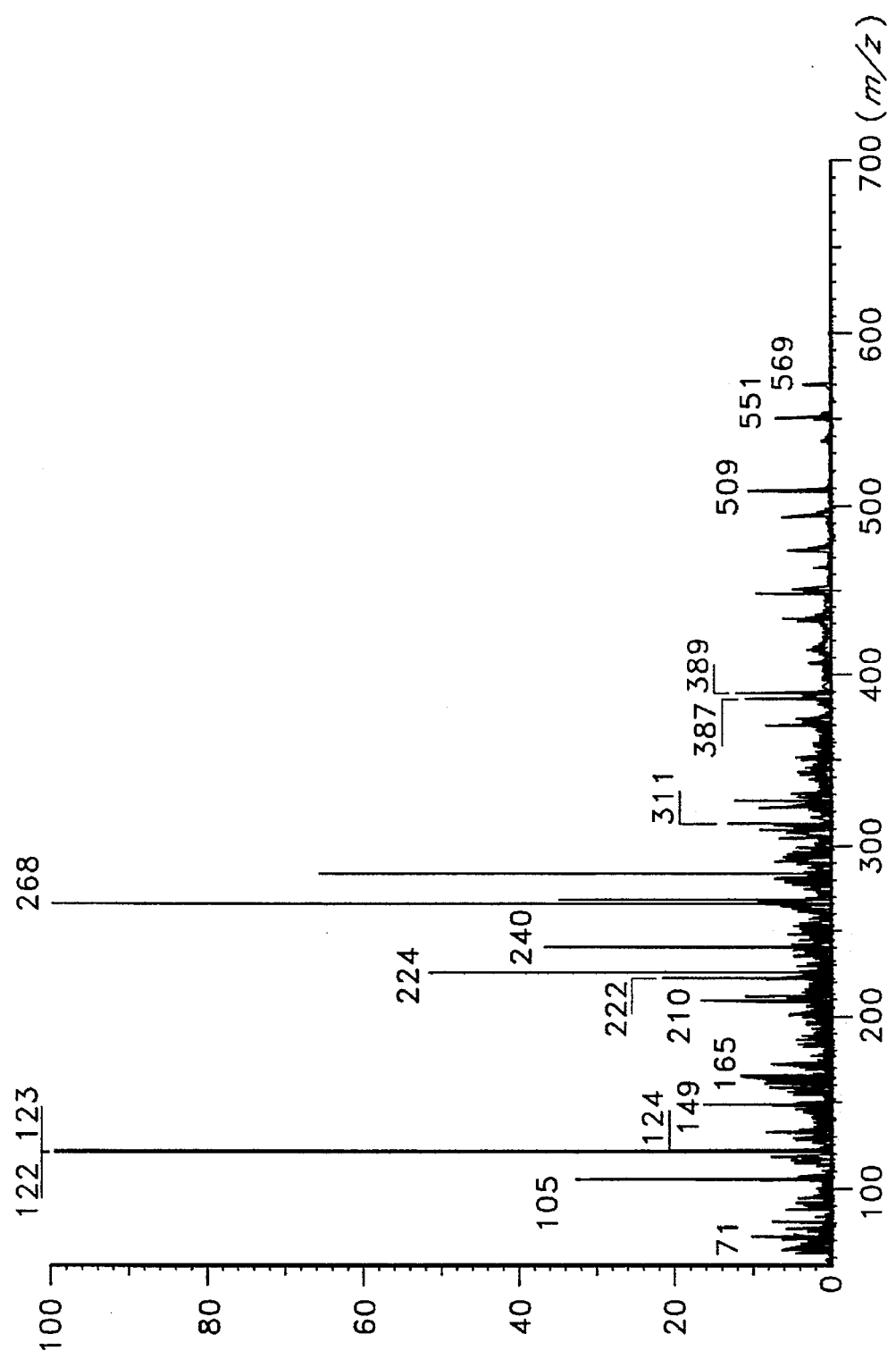
FIG. 9 is a DCI-MS of paclitaxel obtained from this invention.
Figure 10:
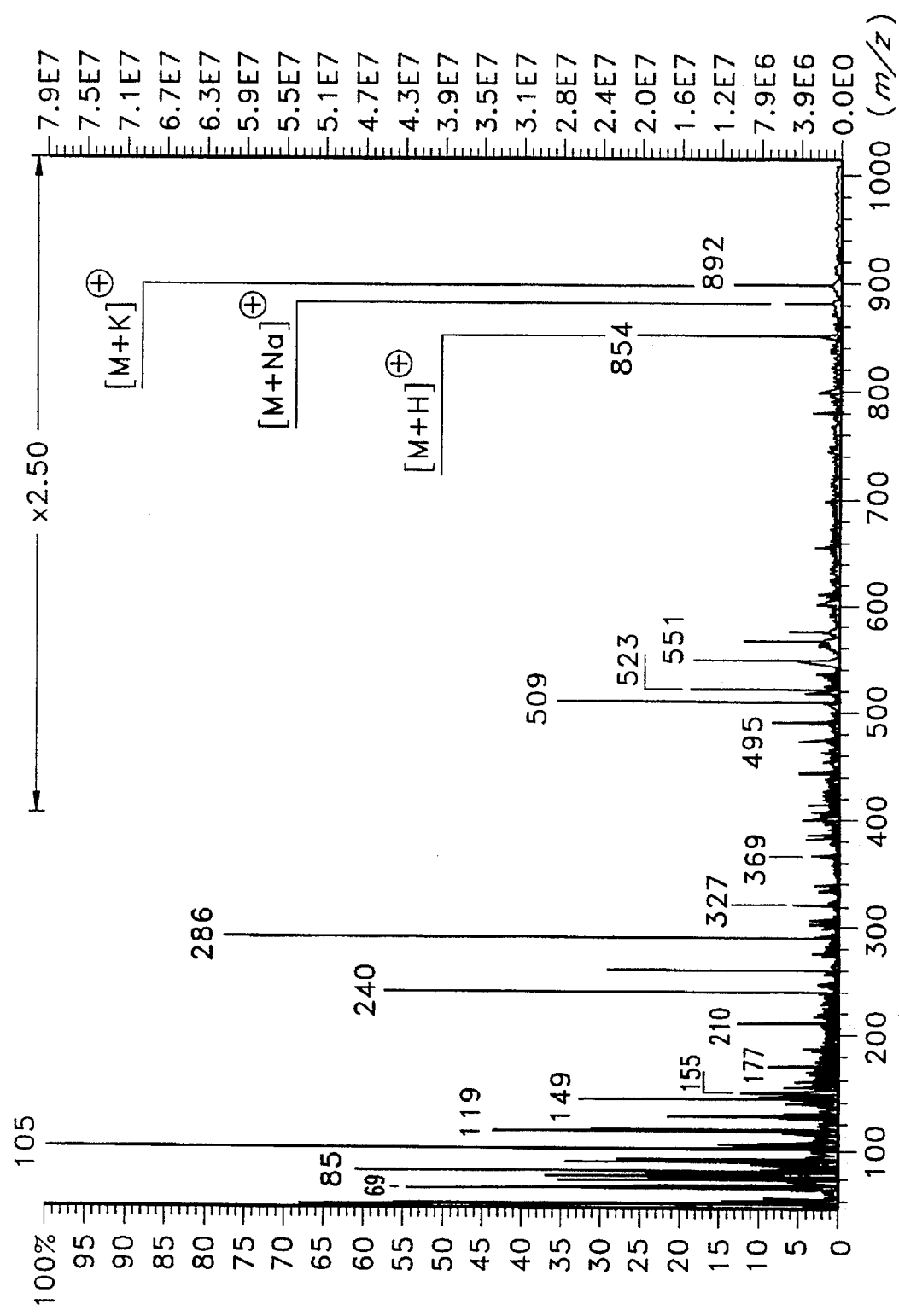
FIG. 10 is a FAB-MS (positive ion mode) of paclitaxel obtained from this invention
Figure 11:
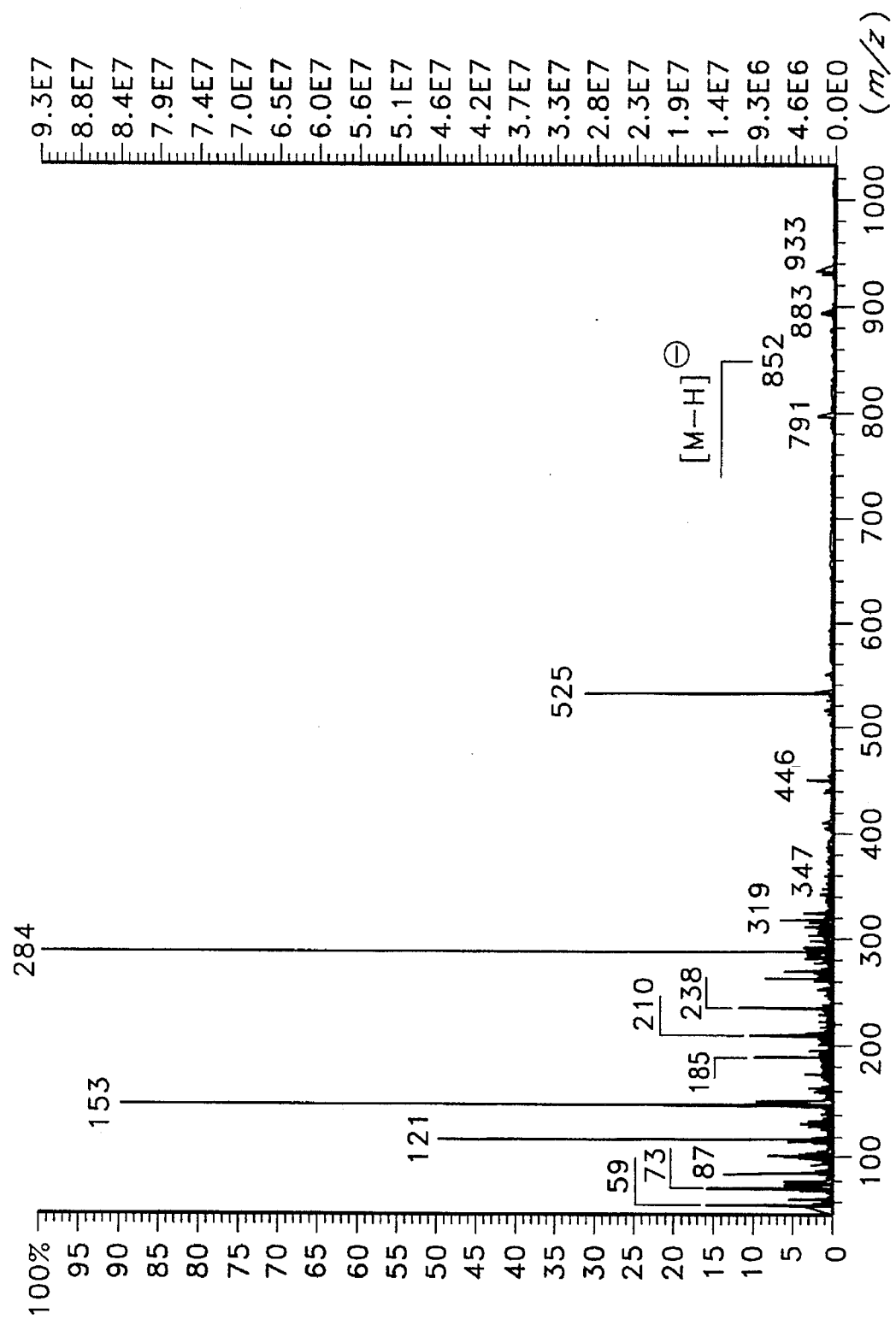
FIG. 11 is a FAB-MS (negative ion mode) of paclitaxel obtained from this invention.
Figure 12:
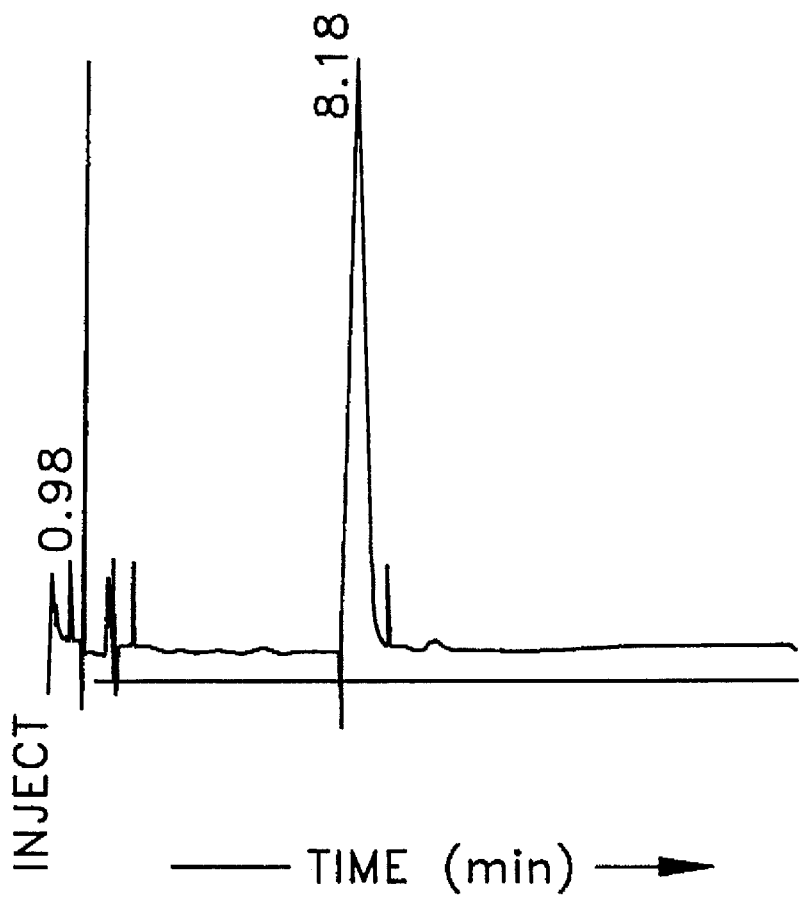
FIG. 12 is a HPLC analysis of paclitaxel obtained from this invention.
Figure 13:
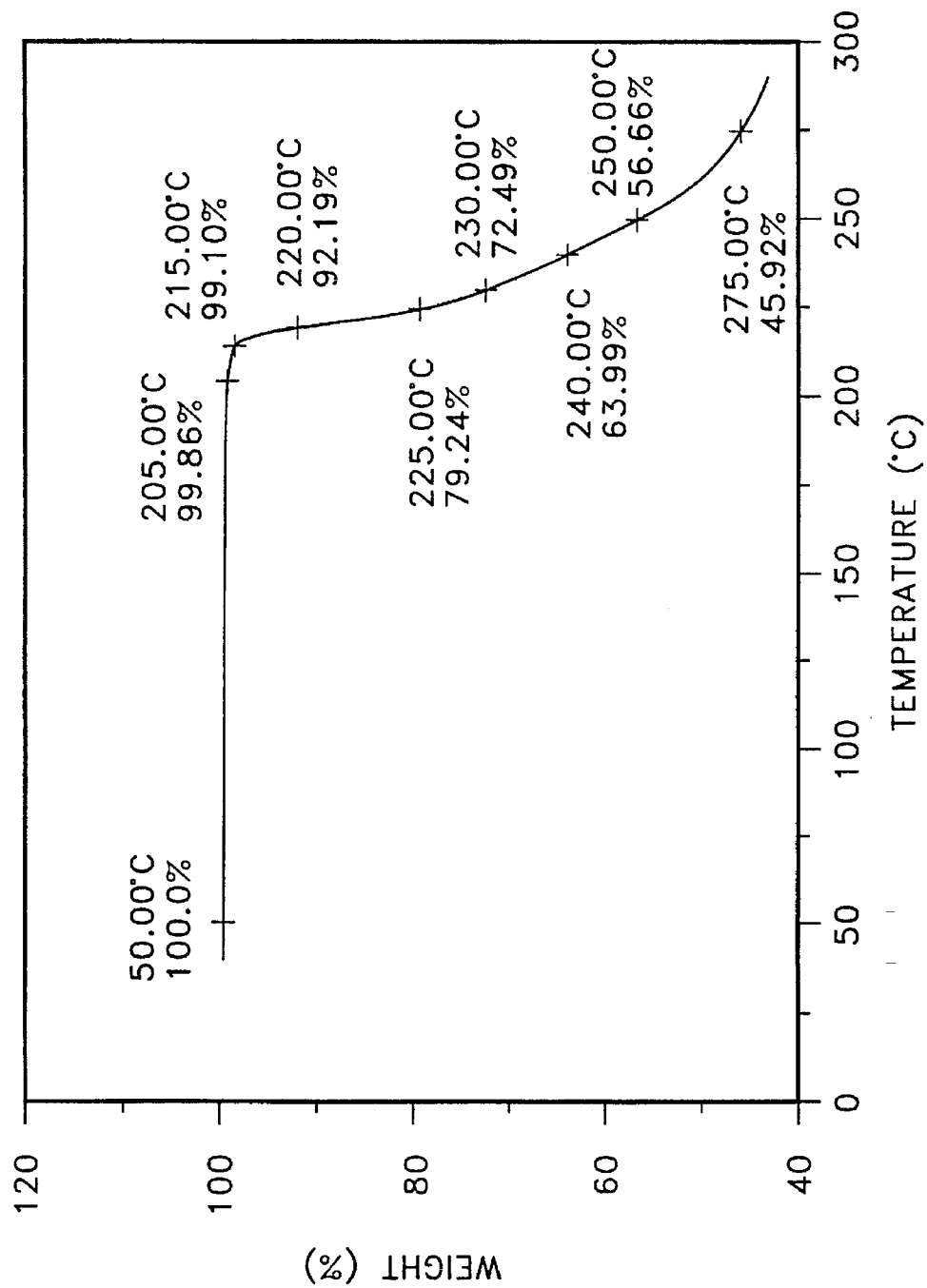
FIG. 13 is a TGA spectrum of paclitaxel obtained from this invention.
Figure 14:
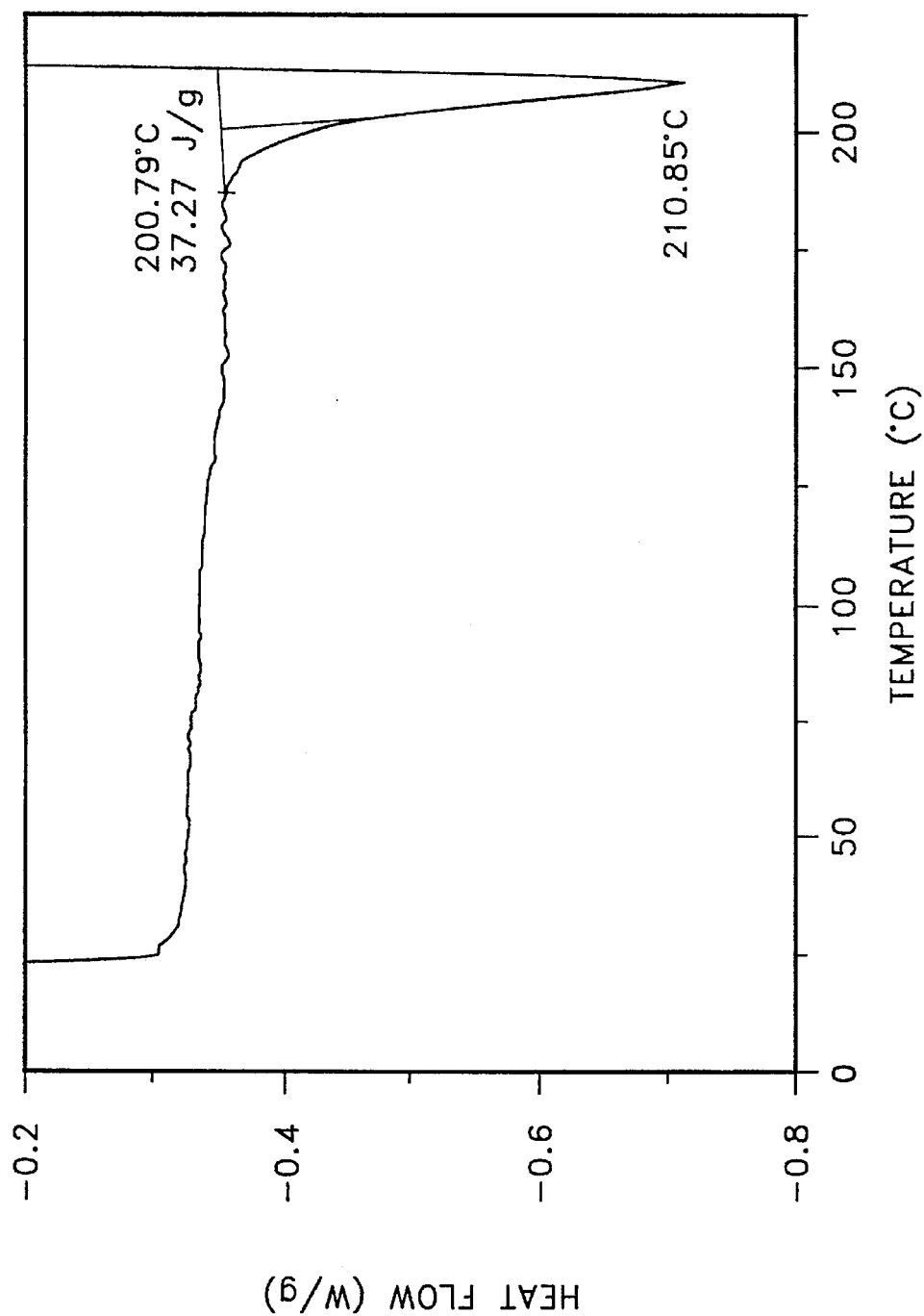
FIG. 14 is a DSC spectrum of paclitaxel obtained from this invention.

| | |
|---|---|
| (300 MHz; CDCl₃) (ppm) | 2.38(S, 3H, CH₃COO at C-4); 4.94(dd, 1H, C-5); 1.88(ddd, 1H, C-6); 2.48(ddd, 1H, C-6); 2.53(d, 1 OH, C-7); 4.38(dd, 1H, C-7); 6.27(S, 1H, C-10); 2.23(S, 3H, CH₃COO at C-10); 6.20(qt, 1H, C-13); 2.27(ddd, 1H, C-14); 2.33(dd, 1H, C-14); 1.13(S, 3H, C-17); 1.23(S, 3H, C-18); 1.78(S, 3H, C-18); 1.68(S, 3H, C-19); 4.20(dd, 1H, C-20); 4.30(S, 1H, C-20); 3.77(S, 1H, C-2'); 4.78(ddd, 1H, C-2'), 5.20(ddd, 1H, C-3'), 7.10(d, 1H, N-1); 7.30 ÷ 7.53(m, 10H, p- & m- protons at aromatic rings A₁, B₁, & C₁); 7.64(t, 1H, A₁-p); 7.72(dd, 2H, C₁-o); 8.11(dd, 2H, A₁-o). |
| FIG. 7b | |
| ¹³C NMR Spectrum (300 MHz, CDCl₃) (ppm) | 79.1(C-1); 75.1(C-2); 45.8(C-3); 81.2(C-4); 84.4(C-5); 35.6(C-6); 72.1(C-7); 56.7(C-8); 203.6(C-9); 75.6(C-10); 133.3(C-11); 141.9(C-12); 72.3(C-13); 35.7(C-14); 43.2(C-15); 21.8(C-16); 26.9(C-17); 14.7(C-18); 9.5(C-19); 76.5(C-20); 73.3(C-2'); 55.1(C-3'); 20.7(CH₃CO) at C-10); 22.6(CH₃CO at C-4); 170.3(CH₃CO at C-10); 171.1(CH₃CO at C-4); 167.0(ArCO – A₁); 167.0(ArCO – C₁); 172.7(PhISCO—); 129.3(aC – C₁); 133.8(aC – B₁); 138.1(aC – C₁); 130.3(o-C, A₁); 127.0(o-C, B₁); 127.0(o-C, C₁); 128.7(m-C, A₁); 128.6(m-C, B₁); 129.0(m-C, C₁); 133.6(p-C, A₁); 131.9(p-C, B₁); 128.3(p-C, C₁). |
| FIGS. 8a and 8b | |
| EIMS: [M]⁺ = 853 (m/z, the main fragments) | 568[T]⁺; 550[T – H₂O]⁺; 508[T – AcOH]⁺; 490[T – AcOH – H₂O]⁺; 448[T – 2AcOH]⁺ or [T – BzOH]⁺; 386[T – AcOH – BzOH]⁺; 326[T – BzOH – 2AcOH]⁺; 308[326 – H₂O]⁺; 286[M – T]⁺ or [S]⁺; 280; 268[S – O]⁺; 240[S – O – CO]⁺; 210[S – O – CO – HCOH]⁺; 122[BzOH]⁺; 105[Bz]⁺; 91[C₇H₇]⁺; 77[C₆H₅]⁺; 51; 43[Ac]⁺. |
| FIG. 9 | |
| DC/MS: [M + H]⁺ = 854 (m/z; the main fragments) FIG. 10 | 569; 551; 509; 492; 449; 387; 327; 311; 287; 269; 240; 224; 222; 210; 165; 149; 123; 105; 92; 71. |
| FAB⁺ MS (m/z; the main fragments) FIG. 11 | 892[M + K]⁺; 876[M + Na]⁺; 854[M + H]⁺; 569; 551; 523; 509; 495; 369; 327; 286; 240; 210; 277; 155; 149; 119; 105; 85; 69. |
| FAB⁻ MS FIG. 12 | 852[M – H]⁻ |
| HPLC | |
| Column Solvent System Flow Rate Detector Injection volume FIG. 13 | μBondapak Phenyl CH₃CN:CH₃OH:H₂O — 32:20:48 1 mL/min Waters 490 at 227 nm 20 μL |
| TGA: FIG. 14 | Temperature (stability): 50.00° C. (100.0%), 205.00° C. (99.86%), 215.00° C. (99.10%), 220.00° C. (92.19%), 250.00° C. (56.66%), 275.00° C. (45.92%). |
| DSC: Water content (% H₂O): | 210.85° C. 0.90% (Karl Fischer) |

We claim:

1. A method for the isolation and purification of paclitaxel from organic material comprising a mixture of taxanes including paclitaxel and cephalomannine; said process comprising;

(1) extracting a composition comprising paclitaxel and cephalomannine from said organic material;

(2) chromatographically separating a mixture comprising paclitaxel, cephalomannine and other taxanes from said composition; then (3) reacting said mixture with a halogen under conditions effective for the selective conversion of cephalomannine to a diasteromeric mixture of 2",3"-dihalo-cephalomannines; then (4) separating said paclitaxel from said mixture.

2. The method of claim 1 wherein the organic material is extracted with a first extraction solvent which is then evaporated to form a first paclitaxel-comprising residue, then extrating said first residue with a second extraction solvent which is then evaporated to form a second paclitaxel-comprising residue, the further purifying said second residue by crystallization.

3. The method of claim 2 wherein said first extraction solvent is methanol and wherein said first paclitaxel-comprising residue is partitioned between water and a solvent selected from the group consisting of methylene chloride, ethylene dichloride and chloroform, and said residue is extracted in said solvent and dried to said second residue, and said second paclitaxel-comprising residue is dissolved in acetone and non-polar impurities are precipitated out with hexanes, wherein the acetone-hexanes solution is then evaporated to about one-third (⅓) volume to form a third paclitaxel-comprising viscous residue.

4. The method of claim 3 wherein said solvent and water are present in about a 1:1 v/v ratio.

5. The method of claim 3, wherein said third viscous residue is precipitated by addition of about ten times volume of hexanes to form a light yellow precipitate to form a fourth paclitaxel-comprising solid residue.

6. The method of claim 4, further comprising dissolving said fourth solid residue in acetone with methylene chloride and/or ethylene dichloride, which is then flash chromotographed over a silica gel column in a chromatographic solvent to obtain fractions of elutant containing mixtures of paclitaxel and cephalomannine which are combined and dried to form a fifth paclitaxel-comprising residue.

7. The method of claim 6 wherein said chromatographic solvent is a mixture of acetone and methylene chloride or ethylene dichloride in about a 1:9 to about 3:7 v/v ratio.

8. The method of claim 6 wherein, said fifth residue is dissolved in a chlorinated solvent selected from the group consisting of $CCl_4$, $CHCl_3$ $C_2H_4Cl_2$ and $CH_2Cl_2$ and reacted with a halogen.

9. The method of claim 8 wherein said halogen is bromine.

10. The method claim 9 wherein said bromine is present at a concentration of from about 0.01M to about 0.1M solution in halogenated solvents.

11. The method of claim 10 wherein reaction with bromine is carried out at a temperature ranging from about $-20°$ C. to about $20°$ C. in the dark.

12. The method of claim 11 wherein substantially all of cephalomannine present in said solution of chlorinated solvents is converted to a diastereomeric mixture of dibromocephalomannines, and paclitaxel is then separated from said reaction mixture.

13. The method of claim 12 wherein said paclitaxel-comprising organic matter is selected from the group consisting of the bark of *Taxus brexifolia*, a plant material from the taxus species, a cell culture from the taxus species and a paclitaxel-producing fungus.

14. The method of claim 12 wherein said paclitaxel is separated from said reaction mixture by silica gel chromatography with a chromatographic solvent comprising a mixture of acetone and methylene chloride or ethylene dichloride present in a ratio ranging from about 1:9 to about 3:7 by volume.

15. The method of claim 12 wherein said separated paclitaxel is crystallized out with acetone and hexane mixture.

16. A method of separating paclitaxel from a mixture comprising paclitaxel and cephalomannine which comprises the steps of a) reacting said mixture with a halogen at a temperature and for a time sufficient to halogenate substantially all the cephalomannine, and b) separating the paclitaxel from the halogenated cephalomannine.

17. A method of claim 16 wherein the halogen is selected from the group consisting of fluorine, chlorine, bromine and iodine.

18. The method of claim 17 wherein the halogen is bromine.

19. The method of claim 18 wherein the bromine is present at a concentration ranging from about 0.01M to about 0.1M.

20. The method of claim 16 wherein the reaction of a) is carried out at a temperature ranging from about $-20°$ C. to about $20°$ C.

21. The method of claim 19 wherein the bromine is present in a chlorinated solvent selected from the group consisting of $CCl_4$, $CHCl_3$ and $CH_2Cl_2$.

22. The method of claim 21 wherein the chlorinated solvent is $CCl_4$ or $CHCl_3$.

23. The method of claim 16 wherein the reaction of a) is carried out in the dark.

24. The method of claim 16 wherein the separation of b) is carried out by silica gel chromatography in a suitable solvent.

25. The method of claim 24 wherein the solvent is a mixture of acetone and methylene chloride or 1,2-dichloroethane in a ratio by volume of from about 1:9 to about 3:7.

26. The method of claim 25 wherein the paclitaxel-containing fractions are evaporated to a solid residue.

27. The method of claim 26 which further comprises purifying the paclitaxel by crystallization.

28. The method of claim 27 wherein the solid residue is dissolved in acetone.

29. The method of claim 28 wherein the paclitaxel is crystallized out with hexanes.

30. The method of claim 25 wherein paclitaxel is separated from a diasteromeric mixture of 2", 3"- dibromocephalomannine.

31. The method of claim 16 wherein the reaction of a) is monitored by high performance liquid chromatography.

32. The method of claim 16 wherein the mixture is derived from a paclitaxel-containing source.

33. The method of claim 32 wherein the paclitaxel-containing source is selected from the group consisting of the bark of *Taxus brevifolia*, plant material from a Taxus species, a cell culture of Taxus species, and a paclitaxel-producing fungus.

34. A method of separating paclitaxel from a mixture of paclitaxel and cephalomannine which comprises the steps of a) reacting said mixture with bromine at a temperature and for a time sufficient to brominate substantially all of the cephalomannine, and b) separating the paclitaxel from the brominated cephalomannine.

* * * * *